United States Patent
Walker et al.

(10) Patent No.: US 11,636,455 B2
(45) Date of Patent: Apr. 25, 2023

(54) INTELLIGENT PATIENT BILLING COMMUNICATION PLATFORM FOR HEALTH SERVICES

(71) Applicant: Inbox Health Corp., New Haven, CT (US)

(72) Inventors: Lawrence Blake Walker, Guilford, CT (US); Simon Kaluza, East Haven, CT (US); Charles Gamble, Woodbridge, CT (US); Kevin Yuliawan, Milford, CT (US)

(73) Assignee: Inbox Health Corp., New Haven, CT (US)

( * ) Notice: Subject to any disclaimer, the term of this patent is extended or adjusted under 35 U.S.C. 154(b) by 191 days.

(21) Appl. No.: 16/510,384

(22) Filed: Jul. 12, 2019

(65) Prior Publication Data
US 2020/0019946 A1    Jan. 16, 2020

Related U.S. Application Data

(60) Provisional application No. 62/697,038, filed on Jul. 12, 2018.

(51) Int. Cl.
*G06Q 20/14* (2012.01)
*G16H 10/60* (2018.01)

(52) U.S. Cl.
CPC ............. *G06Q 20/14* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 6,098,052 A | 8/2000 | Kosiba et al. | |
| 6,117,073 A * | 9/2000 | Jones | G06Q 50/22 600/300 |
| 6,757,898 B1 * | 6/2004 | Ilsen | G16H 40/67 600/300 |
| 7,191,150 B1 * | 3/2007 | Shao | G06Q 10/06312 705/38 |
| 7,519,553 B2 | 4/2009 | Abe et al. | |
| 7,546,262 B1 | 6/2009 | Ferguson et al. | |

(Continued)

FOREIGN PATENT DOCUMENTS

CA    2463305 A1    4/2003

OTHER PUBLICATIONS

De Almeida Filho, Adiel T., Christophe Mues, and Lyn C. Thomas. "Optimizing the collections process in consumer credit." Production and Operations Management 19.6 (2010): 698-708.

*Primary Examiner* — Ayal I. Sharon
(74) *Attorney, Agent, or Firm* — St. Onge Steward Johnston and Reens

(57) ABSTRACT

A system for generating customized patient billing communications includes software executing on a server which receives patient billing data indicative of a patient visit and further indicative of a balance. The software accesses a storage to determine patient visit context data indicative of one or more visit codes associated with the billing data. The software generates a communication for a user based on the patient visit context data with message content altered from a standard message based on the one or more visit codes, the communication including a bill for the balance and being a first communication to the user with the bill.

17 Claims, 11 Drawing Sheets

(56) References Cited

U.S. PATENT DOCUMENTS

| | | | |
|---|---|---|---|
| H2252 H * | 1/2011 | Bohanan | 705/40 |
| 8,135,607 B2 | 3/2012 | Williams et al. | |
| 8,146,807 B2 | 4/2012 | Wellons et al. | |
| 8,165,894 B2 * | 4/2012 | Tawil | G06Q 40/02 705/2 |
| 8,280,761 B1 | 10/2012 | Micek et al. | |
| 8,660,941 B2 | 2/2014 | Willey et al. | |
| 8,762,180 B2 * | 6/2014 | Ghani | G06N 20/00 705/4 |
| 9,049,311 B2 | 6/2015 | Yuzefovich | |
| 9,398,148 B1 | 7/2016 | Neuer, III et al. | |
| 9,690,820 B1 * | 6/2017 | Girulat, Jr. | G06Q 40/06 |
| 9,792,653 B2 | 10/2017 | Gancarz et al. | |
| 10,255,996 B2 * | 4/2019 | Ivanoff | G16H 50/20 |
| 10,340,034 B2 * | 7/2019 | Hyde | G16H 40/67 |
| 10,395,330 B2 * | 8/2019 | Dorris | G16H 20/10 |
| 10,475,142 B2 * | 11/2019 | Hyde | G16H 40/67 |
| 10,528,913 B2 * | 1/2020 | Hyde | G16H 40/67 |
| 10,552,581 B2 * | 2/2020 | Hyde | G16H 20/40 |
| 10,559,380 B2 * | 2/2020 | Hyde | G16H 40/67 |
| 10,679,309 B2 * | 6/2020 | Hyde | G16H 10/20 |
| 2002/0022972 A1 * | 2/2002 | Costello | G06F 19/3418 705/2 |
| 2003/0078881 A1 * | 4/2003 | Elliott | G06Q 40/02 705/39 |
| 2004/0044604 A1 * | 3/2004 | O'Neil | G06Q 40/02 705/35 |
| 2004/0199404 A1 | 10/2004 | Ripperger et al. | |
| 2004/0254816 A1 * | 12/2004 | Myers | G06Q 10/10 705/2 |
| 2006/0190334 A1 | 8/2006 | Smith | |
| 2007/0043659 A1 * | 2/2007 | Kass | G06Q 30/02 705/38 |
| 2007/0294109 A1 * | 12/2007 | Costello | G06Q 50/24 705/3 |
| 2008/0189202 A1 * | 8/2008 | Zadoorian | G06Q 40/06 705/37 |
| 2009/0157435 A1 | 6/2009 | Seib | |
| 2009/0157436 A1 * | 6/2009 | Craycraft | G06Q 10/10 705/4 |
| 2009/0248449 A1 | 10/2009 | Dhillon | |
| 2010/0324924 A1 | 12/2010 | Frederiksen | |
| 2011/0004494 A1 | 1/2011 | Denny, Jr. et al. | |
| 2011/0060671 A1 * | 3/2011 | Erbey | G06Q 40/00 705/35 |
| 2011/0145021 A1 | 6/2011 | Denny, Jr. et al. | |
| 2011/0178817 A1 | 7/2011 | Porter et al. | |
| 2011/0202370 A1 * | 8/2011 | Green, III | G06F 19/328 705/3 |
| 2011/0238435 A1 * | 9/2011 | Rapaport | G06Q 10/10 705/2 |
| 2011/0246225 A1 * | 10/2011 | Green, III | G16H 10/60 705/2 |
| 2011/0301982 A1 * | 12/2011 | Green, Jr. | G06Q 10/10 705/3 |
| 2011/0313784 A1 * | 12/2011 | Harvey | G16H 80/00 705/2 |
| 2012/0143620 A1 | 6/2012 | Linetsky et al. | |
| 2012/0239417 A1 * | 9/2012 | Pourfallah | G06Q 20/384 705/2 |
| 2012/0253868 A1 | 10/2012 | Ach et al. | |
| 2012/0296815 A1 | 11/2012 | Seib et al. | |
| 2013/0159168 A1 | 6/2013 | Evans | |
| 2013/0173302 A1 * | 7/2013 | Hyde | G06F 19/3418 705/3 |
| 2014/0052457 A1 * | 2/2014 | Tover | G06Q 50/22 705/2 |
| 2014/0074500 A1 | 3/2014 | Seib et al. | |
| 2014/0188508 A1 * | 7/2014 | DeFrank | G06F 19/328 705/3 |
| 2014/0222716 A1 | 8/2014 | Joplin | |
| 2015/0193749 A1 * | 7/2015 | Ivanoff | G06Q 20/14 705/40 |
| 2015/0220860 A1 * | 8/2015 | Perepa | G06Q 10/0633 |
| 2016/0124920 A1 * | 5/2016 | Golay | G06Q 10/10 705/3 |
| 2016/0283676 A1 * | 9/2016 | Lyon | G06F 19/328 |
| 2016/0321624 A1 | 11/2016 | Brunner | |
| 2017/0116373 A1 * | 4/2017 | Ginsburg | G16H 40/20 |
| 2018/0081859 A1 * | 3/2018 | Snider | G06F 40/10 |
| 2018/0308569 A1 * | 10/2018 | Luellen | G16H 40/20 |
| 2019/0005421 A1 * | 1/2019 | Hammel | H04M 3/5175 |
| 2019/0189253 A1 * | 6/2019 | Kartoun | G16H 50/30 |

* cited by examiner

INTELLIGENT PATIENT BILLING COMMUNICATION PLATFORM FOR HEALTH SERVICES

FIELD OF THE INVENTION

The following relates to enhanced and tailored communications usage and contextualization of messaging for medical billing. More particularly, the present invention utilizes machine learning to select appropriate communications channels and communications in order to more efficiently collect payment for medical bills.

BACKGROUND OF THE INVENTION

While there are a number of existing methods to manage patient appointments, handle patient billing and collection through the appointment process electronically, these are often cumbersome and difficult to use and rigid in their approach. They try to fit all patients into a single category and address them all the same way which is not realistic and prone to problems that leads to a lack of adoption by patients, frustration on the side of both patients and doctors, and ultimately a lack of success in interacting with patients for appointments, follow-ups, and lack of collection for billing.

For example, a patient may be sent an incorrect paper statement in the mail as a result of a change in insurance coverage. This can lead to frustration on the part of the patient, and delays in payment for the biller. Additionally, a patient who opts to receive electronic billing notices may be unresponsive to them or they may be caught by a spam filter, but the existing billing system will not adequately address their change in responsiveness and modify the next steps in the process.

Further, patients are certainly not a one size fits all. There is so much variety that trying to cater to all with a middle of the road solution will only frustrate everyone. It is important to customize and vary the approach depending on not just general demographics but also to the individual and their preferences including but not limited to psychographic segmentation.

This customization and personalization is becoming mainstream in almost every area in our lives. From custom restaurant orders to custom running shoes, coffee cups, and insoles made on demand, consumers are expecting a level of flexibility and individualization in their relationships with providers of all kinds. When it comes to healthcare it is naturally far more important to ensure good communications than it would be or shoes or a meal. This is in the best interest of everyone involved.

The cost of healthcare continues to grow, often rising to one of the most expensive line items in a given household's budget. In some cases, financial strain puts people in a situation where they must choose between healthcare and food or rent, resulting in neglect of preventative care or follow-up care. Patients will often not admit or even accept the reality of such a situation and become reluctant or embarrassed to share this information with their providers. In such situations, knowing the realities of the patient's financial situation may allow a billing user to adjust and recommend cost effective choices for care.

Insurance plans are also undergoing frequent changes as new policies and regulations take effect. These plans and policies are increasingly complex and difficult to understand for all but experts in the field. Doctors and medical facilities typically take patients both with and without insurance. In both cases, there can be many unknowns when it comes to the out of pocket cost for a given patient. Physicians and their staff, or the staff of a third party billing entity acting on the physician's behalf, spend a lot of time on the phone following up with patients, family and other caregivers to coordinate billing and payment with patients. Much of this time is spent dealing with billing questions and insurance questions. This simply increases the operational cost of running a practice, and contributes a large amount towards wasted administrative costs in healthcare. Collecting and following up with patient billing can also be difficult and there are often high rates of write-offs and non-payments which remain uncollected or get sold off at a discount to collection agencies.

Patients are understandably concerned about fees and bills and, when going to see a medical practitioner, they often worry about surprises which come about as additional fees and potential non-coverage by insurance. In some cases, bills come from multiple billers and a patient may receive bills from many individuals and departments that participated in their care. For example, an anesthesiologist, a lab that did blood work or pathology, X-rays or other tests are typically charged in addition to the doctor's fees from the practice itself.

In many cases, physicians outsource billing to a third party billing agency. However, the physician's office is still responsible for collecting billing contact information, copayments at the time of care, and is responsible for collecting appropriate authorizations from the patient for billing matters. This can often only be done through paper based processes, and requires the use of dated technology like fax machines to send patient information to the billing company. This is because the physician's office software is not capable of communicating some information, such as copayments, communication preferences, or credit card information, to the software used by the third party billing agency's software. This manual, paper process often leads to lost information, such as misplaced copayment records. This is the cause for many patients to receive incorrect bills for amounts that they have already paid.

SUMMARY OF THE INVENTION

A system that allowed the physician's office to collect patient copayments, credit card information, and contact preferences at the time of care, that is capable of digitally transmitting this information to the third party billing agency's software, would meaningfully improve the administrative efficiency, and improve the accuracy of patient billing.

A system that is capable of simplifying the estimation and billing process for patients and bundling these fees together into an easy to read and easy to understand comprehensive and complete estimate and subsequent invoice would be beneficial. Such a system that is further capable of detecting financial strain on patients and of alerting the practice to this strain would also be beneficial.

Accordingly, a system that applies machine learning to the domain and is capable of determining more efficient and/or preferred methods of communicating with and billing patients would be useful and desirable. Such a system, capable of adapting in real time to incorporate feedback and success of the approaches tried, would be highly desirable.

Additionally, a system that is capable of automatically answering patient questions about their medical bills using SMS, email, internet chat software, physical mail, or through the use of an interactive voice response system, would be highly desirable to patients, as their questions would be answered more quickly. This would also reduce overhead in the patient billing process.

Therefore, it is an object of the present invention to communicate medical bills to patients both initially and in follow up collection attempts in a more efficient manner.

It is further an object of the invention to customize and contextualize messages to provide explanations and/or requests for information from the patient which could enable more efficient communications, payment and may allow for collection of the bill from an insurance carrier instead of out of the patient's pocket.

It is a further object of the invention to provide for interactive messaging in a number of different forms and use those forms, depending on the preferences, communications history and medical history of the patient.

It is another object of the invention to provide a system and method for simplifying and improving the success of billing and communication with patients that adapts and learns on an individual patient by patient basis and anticipates and resolves common questions and concerns.

For this application the following terms and definitions shall apply:

The term "biller" as used herein means any user interested in the billing process from an entity such as a third party billing provider, administrator, a practice, an independent doctor's office, a hospital, insurance company, or other entity interested in the billing practices of said entity.

The term "provider" as used herein means any entity such as a third party billing provider, a practice, an independent doctor's office, a hospital, insurance company, or other entity providing services to the patient.

The term "network" as used herein includes both networks and internetworks of all kinds, including the Internet, and is not limited to any particular network or inter-network.

Objects of the invention are achieved by a patient communications system having a storage containing contact data related to the plurality of patients, the contact data indicative of communications habits of the plurality of patients as related to bill collection success. Software executes on a computer and the software includes a patient data module which receives patient data including contact and insurance information and demographic information for a plurality of patients, one of which is associated with a user. The software further includes a defaults module which queries the contact data and patient data to determine a rank order of communications methodologies based on the communications habits of the plurality of patients as compared to the demographic information. The software further includes a history module which queries the storage by the user to determine modifications to the rank order of communications based bill collection success for the user. The software includes an insurance adjudication module which queries an insurance adjudication result to determine one or more codes which are related to a bill associated with the user. The software also includes a medical module which queries the bill based on one or more patient treatment codes associated with a change in likelihood of one or more communications modules being successful, the medical module updating the rank order if the one or more patient treatment codes indicate a change in likelihood with one or more communications methodologies in the rank order of communications. The software also includes a communications module which generates a bill communication for the user to transmit the bill to the user and further modifying a content of the bill communication based on the one or more codes to request information from the user if the one or more codes indicate that patient data from the user is missing which could modify the bill.

In certain aspects the software includes a data module and the bill communication is sent to the user using a first communications methodology from the rank order of communications and the storage is updated by the data module based on if the bill is paid. In other aspects, if the bill is not paid, the bill communication is sent to the user using a second communications methodology from the rank order of communications and the storage is updated by the data module based on if the bill is paid following communication of the bill to the second communications methodology and the storage is updated by the data module based on the first communications methodology being unsuccessful. In certain aspects, the software includes a data module and the tool is in communication with a plurality of external billing systems, the data module extracting data from the plurality of external billing systems and transforming the extracted data to a unified format. In certain aspects the data extracted to the unified format is stored in the storage. In other aspects the contact data and the data extracted is stored in the storage in the unified format. In other aspects the user is one of the plurality of patients. In still other aspects when the one or more codes indicates denial of a claim based on expired or incorrect insurance information, the message content includes a request for updated insurance information from the user. In still other aspects the software modifies a communications methodology for the communication based on the one more patient treatment codes.

Still other objects are achieved by providing a system for generating customized patient billing communications. The system includes software executing on a server which receives patient billing data indicative of a patient visit and further indicative of a balance. The software accesses a storage to determine patient visit context data indicative of one or more visit codes associated with the billing data. The software generates a communication for a user based on the patient visit context data with message content altered from a standard message based on the one or more visit codes, the communication including a bill for the balance and being a first communication to the user with the bill.

In certain aspects the one or more visit codes include one or more insurance adjudication codes which are indicative of how the balance was determined. In other aspects the one or more insurance adjudication codes indicates denial of a claim based on expired or incorrect insurance information, the message content includes a request for updated insurance information from the user. In still other aspects the one or more visit codes include one or more patient treatment codes and the software modifying a communications methodology for the communication based on the one more patient treatment codes. In yet other aspects the software modifies the communication methodology to delay sending the communication based on the one more patient treatment codes. In other aspects the user is associated with a rank order of communications methodologies of anticipated bill collection success and the software determines a modified rank order based on the one or more patient treatment codes. In still other aspects the rank order of communications methodologies and modified rank order are determined by the software based on the patient billing data. In yet other aspects the patient billing data is obtained from a plurality of external billing systems and the software transforms the patient data obtained from the plurality of external billing systems into a unified format, such that the patient billing data is stored on the storage in the unified format. In other aspects the rank order of communications is determined by the software by comparing patient billing data of the user to other patient data based on one or more matching demographic categories. In yet other aspects the storage is updated based on the user's communications history as related to collection success. In yet other aspects the software receives at least some of the patient data from one or more external billing systems in one or more formats and stores the patient data in the storage in a unified format.

Other objects are achieved by providing a patient billing communication system comprising software executing on a computer which provides a portal for access by one or more users. The portal allows the one or more users to access billing information using personal information and security tokens as their authentication key. The portal contains demographic, insurance, clinical, and billing data regarding users, obtained through integrations with practice management, billing, and health record systems or subsystems. The software determines a series of dynamic billing events constituting a dynamic billing algorithm for each of the one or more users based on a set of conditions such as the insurance adjudication, associated medical providers, demographics, and preferences then associating each user with a billing cycle. The billing events contain one or more possible communication methodologies selected from the group consisting of: SMS text, email, voice calls, social media messaging applications, and paper mailed notices. The software queries the user data and the conditions to determine whether or not each billing event should be performed. The software receives an indication of payment of the bill and associates the indication with a communication methodology associated with the default communications which resulted in the indication. The software updates a user profile for at least one of the one or more users to be a revised version of the default communications profile including a rank order of communications based on the communication methodology being higher in sequence due to the indication for at least one of the one or more users. The software updates a database of user profiles so that the default communication profile is determined based on a statistical analysis of the user profiles in the database and updating of the database modifies the statistical analysis such that as user profiles of particular demographics change, the default communication profile for that particular demographic changes. The dynamic billing algorithm utilizes machine learning by altering the billing events of each individual user's billing cycle by weighting results and conditions of similar user demographic profiles using prior billing cycles as inputs for said dynamic billing algorithm.

In certain aspects a scheduling module is the portal and enables the one or more users to schedule a visit that tailors the communication and user experience based on the progress and results of their current and prior state in the dynamic billing algorithm. The software receives an indication of visit services and the software also receives payment information from the one or more users, the payment information includes one or more of insurance information and payment method. The software generates an estimate of costs associated with the services and generates a billing estimate for the one or more users prior to the visit to indicate a user contribution for the one or more users associated with the services. The software receives an authorization to charge the payment method based on an estimate of cost. The billing events also contain other actions to the patient user's account, including actions selected from the group consisting of referring to collections, requesting a staff review, writing off a balance, pushing or pulling data from external systems, offering discounts or payment plans to patients, customizable database operations and combinations thereof.

In other aspects a system is provided including a healthcare specific artificial intelligence agent that utilize natural language processing to parse user responses and extract particular healthcare billing information into a common database structure in order to automatically respond to common medical billing questions, evaluate conditions and criteria and create billing events, and flags them for further review and customer support. The user responses are selected from the group consisting of: automated voice, chat, email, text, forms of electronic communication and combinations thereof. The system normalizes user responses into a centralized ticket system for tracking and resolution.

In certain aspects the system includes an interactive voice response system capable of receiving telephone calls from patient users that can parse the user's input, either through recognition of the user's speech, or recognition of the user's entries into their telephone keypad. The responses can be parsed to confirm a patient user's identity by matching the incoming phone number which dialed the interactive voice response system, and one to two other pieces of personal information. The responses can further be used to provide a confirmed patient user's with additional information about their billing account, such as their balance, insurance claim status, or appointment status. The responses can additionally prompt the patient user to provide additional information, such as updated insurance information, additional contact information, or credit card information for payment.

In other aspects a billing system software is provided including a server which communicates with both practice management systems and insurance clearinghouses to normalize and reconstruct a full patient profile from disparate sources to create a reconstructed profile. An identity matching protocol combines billing data related to the same patient but sourced from the disparate sources. The reconstructed profile is fed into a billing cycle management software in a platform independent format and is acted upon to communicate with users.

In certain aspects the profile along with its associated billing events, cycles and machine learning meta-data is stored on a public and/or private blockchain network for auditability and interoperability.

Other objects are achieved by providing a server with software executing thereon which allows billing entities, which use multiple disparate systems within their businesses to bill insurance, to integrate existing systems and workflows for the transmitting of patient bills, communications, and payments of medical bills, the software communicates with specialized credit card readers in each physician's office to accurately record and allocate payments to the billing entity's relevant systems in an automated way. A centralized web service receives phone calls, tickets and notes related to patient data and billing information in said disparate systems, and distributes relevant information back to relevant billing users and the external disparate systems.

In one embodiment, the systems and methods may provide the most efficient and most desirable communications means with the patient to provide billing information and to collect bill payments.

In another embodiment, the systems and methods may allow for the reduction in cost which includes the reduction of paper bills and their mailing, a timelier collection interval, and a decrease in written off or unpaid balances or transfers to collection agencies.

In yet another embodiment, the systems and methods may save the patients money by offering incentives to prepay, pay in a timely manner, or to provide credit card information during registration for auto-payment.

In yet another embodiment, the systems and methods may help detect payment duress or inability to pay of certain customers and to provide this feedback to the practice so that doctors can be aware of a patient's situation and make informed recommendations for their care.

Other objects of the invention and its particular features and advantages will become more apparent from consideration of the following drawings and accompanying detailed description.

DETAILED DESCRIPTION OF THE INVENTION

Figure 1:
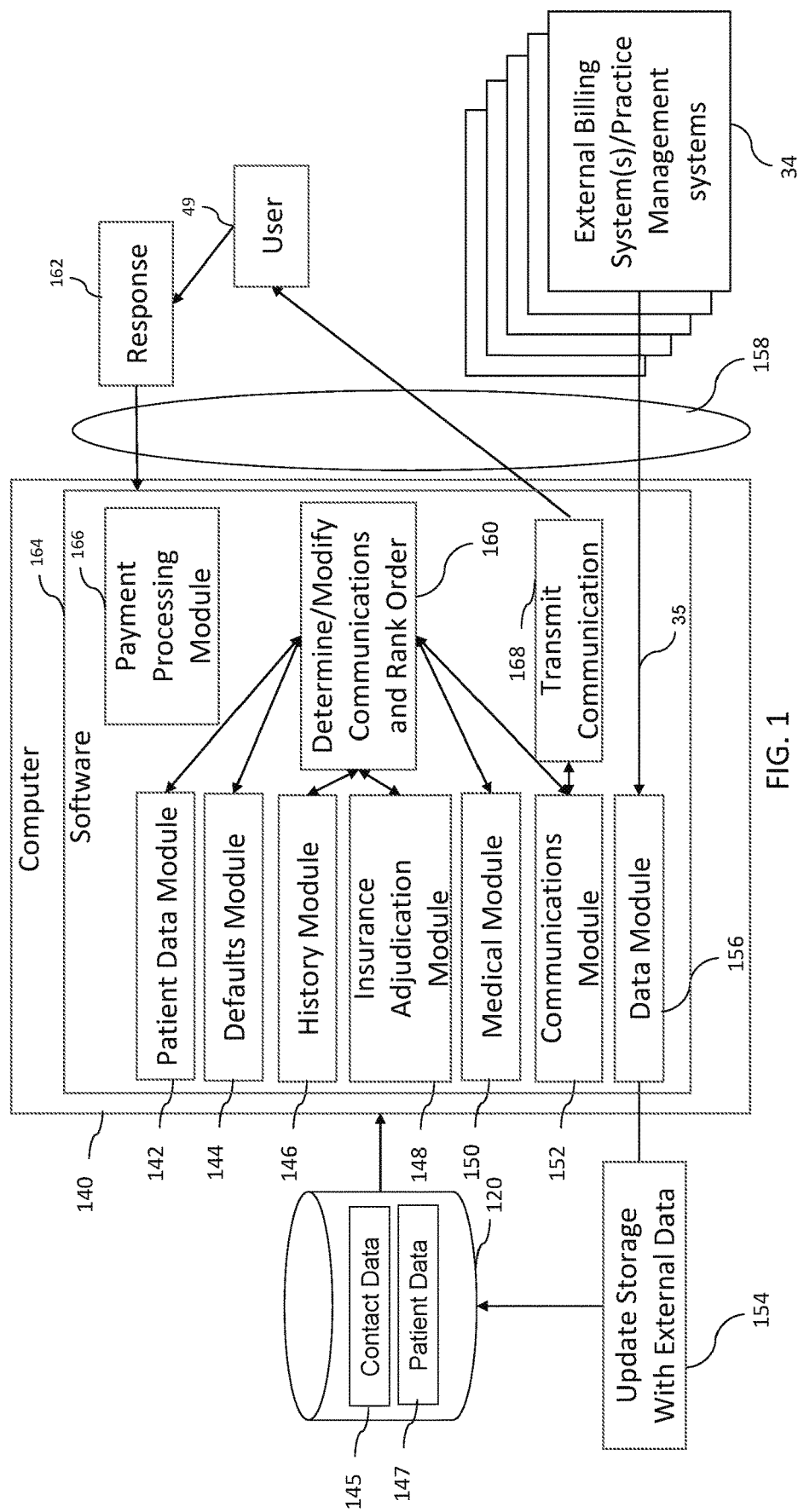
FIG. 1 is a functional flow diagram showing the generation, modification and transmission of patient communications according to the present invention.

Referring now to the drawings, wherein like reference numerals designate corresponding structure throughout the views. The following examples are presented to further illustrate and explain the present invention and should not be taken as limiting in any regard.

FIG. 1 shows computer 140 with software 164 executing thereon. It is understood that the computer can be one or multiple separate computers, servers and other computing devices and can include virtualized machines which operate on distributed processing power. The software provides a number of modules which generate and optimize patient communications and bill collection success. The patient data module 142 obtains information from a number of patients which is stored in storage 120. This storage may be local or network accessible storage(s) and can include e.g. contact data 145 and patient data 147. The contact 145 and patient 147 data are understood to be but two examples of the types of data accessible to the software 164 on the storage(s) 120. It is understood that data shown throughout the other figures can be included as part of the contact and/or patient data. The contact data allows the software to determine the communications patterns of the user as related to bill collection success. For example, if previous attempts to e-mail a bill were un-successful but a SMS communication worked, the contact data 145 would indicate this to the history module 146. The patient data module 142 can use the data on the storage 120 in order to determine billing events and queue billing actions 42, billing events 53 and altered billing events 57.

Demographic information of the user 49 can be looked at using the defaults module 144 Particularly, information such as age, gender, income, ethnicity and other such information of the user is obtained in the patient data module 142 and is used to compare the particular user 49 to similar demographics of a number of patients to determine an order of communications which are likely to work based on the user's demographic by comparing to patient data 147 (which it is understood that the user 49 contact data 145 can be a subset of the patient data 147 which is all contained within one database or multiple related databases). This allows default rank order of communications 160 to be determined by the default module 144. This order is adjusted by the history module 146 which looks at the specific user's interactions with communications, particularly billing and medical billing communications to determine if the user 49 tends to deviate from the default module 144 rank order 160 which would indicate a modification 160 is needed. The medical module 150 is used to look at medical codes contained in the patient data 147 which relate to bills the patient owes.

This medical module 150 and the underlying codes may indicate to the system that the user is likely to not receive or respond to a communication sent today due to the procedure the user may have just had and may indicate that a delay in sending the communication is appropriate based on the medical condition of the user. In addition, the rank order 160 for the user prior to a particular communication may, based on their medical condition and the medical module, associate particular treatment codes with an increased or reduced likelihood that a particular communications methodology will work. For example, if the user has a hearing or sight problem which has either developed or was recently treated, this could indicate a change in likelihood that written or oral communications are more or less likely.

Thus, the communications module 152 takes the foregoing into account both in sending the communication and in determining the content based on contextualized data and information. The software transmits 168 and the user 49 then (presumably) receives the communication which will typically include the first instance of the bill/invoice that the user 49 owes and then a response 162 (or the absence thereof) is monitored. The response 162 may simply be the user paying the bill and recording the paid bill in the patient data 147. In this manner, the patient data when next queried by the software 164 will not result in the same bill being re-generated. If no response 162 is received, the system continues down the rank order 160 of communications in order to elicit a response and continues to transmit 168 communications until the bill is collected or there is some form of manual intervention. The results of this order of communications in terms of success in collecting is updated in the data module 156 which then updates the storage with such types of external data 154. It is also understood that in transmitting the communication 168, there may be delays in sending based on various codes determined by the medical module 150 or based on when the last communication was sent and the expected time for a response 162.

The data module 156 also serves to provide for unified formatting of patent 147 and contact 145 data so that such data is useable by the software 164. The underlying data from external billing systems 34 can be received or gathered by the data module 156 and converted to the unified format for storage 120. The response 162 (or absence thereof) is also associated with the user and the patient data 147 which is likewise updated based on the success (or lack thereof) for particular communications. Thus, the next time e.g. the history module looks at the particular user's communications patterns, a different communications methodology may make its way to the top of the rank order.

The insurance adjudication module 148 determines insurance codes related to a patient balance found in the patient data 147. Thus, if the code indicates a denial due to the patient's insurance being expired, the communication is modified 160 to prominently request that the user 49 provide updated insurance information. Typically, the communication will include the bill post insurance adjudication, but optionally, the communication would not include the bill at the time the updated insurance information is requested and would instead allow the user 49 an amount of time to update their insurance for re-submission. Other insurance codes and their responses can be programmed into the system to associate reasons for denial to possible ameliorative action to either eliminate or reduce the bill amount which the system will ask that the patient take. The storage 120 can contain data associating particular insurance codes or types of insurance codes with different communication content such that if the insurance adjudication module finds certain types of insurance codes (e.g. pay part, denial due to incorrect or no insurance or others) the storage can have associated data to allow the communications module 152 to generate the appropriate communication. It is understood that the data module can receive data from various insurance carriers as part of the external billing systems 34 which is updated to the storage 120 in the unified format, allowing the software to utilize the insurance adjudication results and associated codes to take appropriate action with regards to the user 49 and communications transmitted 168.

The system employs well known functions such as email, SMS, internet-based chat software (e.g. Intercom, Facebook Messenger, Twitter), physical mail, phone calls, etc. to interact with patients, insurance companies, third party billers, and healthcare providers and selects the most appropriate process on a per patient basis. Machine learning later tailors the approach to each patient based on the success and results obtained using prior approaches with other patients who exhibit similarities in demographics, clinical conditions, insurance coverage, or socio-economic status.

While initially a set of demographic, billing history, insurance, and appointment data is used to set defaults in the system, even these defaults adapt over time as the number of participants in the data set grows and sample sizes become larger. As the system learns and gathers more data, sub-categorization of classes can be made, and the defaults applied to new patients are also improved.

For a given new patient, such a system will learn on a personalized basis related to interaction with that specific patient. The system will adapt based on what has worked and what has not, as each interaction is tracked and marked as successful or not. For example, a given patient that has not responded to emails and physical letters, but has replied to an automated phone call, may be approached directly with such a phone call on the next billing event. The system and methods described form a framework for evaluating and selecting an approach among many. As new interaction approaches are developed, the system can test their efficacy against existing interaction approaches.

In addition to ranking of success criteria, the system also employs surveys, sentiment analysis, and other feedback techniques to solicit input from its users and to adjust preferences accordingly. These inputs along with the success criteria are all weighted and used in determining the approach with the highest likelihood for success with the specific patient.

There are many reasons that factor into why individual approaches are necessary to address patients and why such a dynamic and self-tuning system is beneficial. Ultimately, each patient is unique. This applies to their financial situation, their health, their stress and activity level with other obligations, and even their history and background with regards to healthcare, money management or responsibility.

Considering the financial situation of patients, one must consider the patient's ability to responsibly deal with the financial obligations of their care. Some patients may be in a situation where money is no object, and their primary concern is immediate care and the quickest path to a full recovery. They may be open to experimental or supplemental treatments which may or may not be covered by insurance. They would have no qualms about paying for such treatment out of pocket if necessary.

Others may be less fortunate and may have to make key decisions and trade-offs that affect their day to day living expenses in order to pay for their medical care. In these cases, a patient that may be struggling to make ends meet would appreciate having billing options such as ways to pay over time, payments with credit cards or other credit facilities, or even less expensive treatments if feasible. For example, if one is not able to afford long term physical therapy but would be willing to do home exercises which, while perhaps less effective, this option would still be better than no treatment at all.

There are of course many other situations that may impact payment, and these may simply be transitory events like an otherwise financially responsible patient that just had to pay for car repairs or had a family emergency or unexpected financial obligation and now requires some extra time to pay.

The medical practice, of course, also needs to collect its payments in a timely manner to make payroll and cover expenses. They may put incentives in place with such a payment system allowing for discounts for paying early, they may charge interest or penalties for overdue payments. Some practices may even provide a discount simply for having a valid credit card on file which can be used to charge payments automatically.

Doctors are often decoupled from the mechanics of bill collection in their practice and may not realize or know the situation of individual patients, who may in turn be reluctant or embarrassed to divulge any financial hardship. This may be simply out of embarrassment or perhaps even as a concern that they may not receive the care they need should their situation be known. A system that could provide feedback to the practice about patients may give the doctor insights to allow them to provide appropriate care and suggestions in light of this supplemental information.

The method of communications with the patient is also a key factor and just as with financial payment options, communication preferences vary greatly from patient to patient. Some patients may be quite tech savvy and would prefer to enter everything on their mobile devices. Such patients are likely to opt into electronic statements and will react quickly and reliably to text messages or notifications in real time. Other patients may prefer written communications mailed to their physical addresses so that they have tangible paper which they can pick up, read and annotate and put into their filing system. Still others, may keep no records at all and prefer to simply deal with the practice over the phone and will rely on follow-up reminders to get them to show up. No single method or system is ideal for everyone and sending ineffective alerts is costly for the practice and potentially confusing to patients.

In a system that offers a variety of communications methods, one can configure the initial parameters for communications preferences based simply on demographic information. For example, someone who is 80 years old and in poor health, may be configured to receive a phone call and a letter, the option of switching to text or other communications methods can be presented, but it is possible that someone in such a demographic may have only a desktop computer, if at all, and may not have a data capable mobile device.

It is also quite possible that a person in the same demographic, has entrusted their child or a caregiver to help with their medical care, and such a person may have an entirely different set of preferences when it comes to communication about appointments and about billing.

A younger demographic is more likely to respond to text messages and want to manage their appointments and information directly from their mobile device. Such a person may not even have a desktop or laptop unit and may be accustomed to functioning solely with a mobile. It is not atypical to have such a demographic pay directly through a mobile wallet that has been enabled on their mobile phone or mobile device.

There are many distinct reasons someone may choose or prefer a particular communications option. For example, one person may be particularly busy and always on the move. They always have their mobile with them and they use this as a preferred method of communications for everything. This person would likely select electronic communications and would not be interested in paper bills and mail outs which they would be expected to file.

Another person may choose the same options for completely different reasons. An environmentally conscious person who is concerned about recycling paper and their carbon footprint may want to avoid having paper bills or reminders mailed out and opt to have electronic communications simply to avoid the paper waste and the energy used to deliver the paper.

A third person may simply be having trouble with their mail carrier and have had a history of misdelivered mail and does not want to miss paying their bill and causing a disruption to service, or a penalty for late payment. This list can be extended ad infinitum.

It is not the desire of the application to categorize everyone in a particular age group or financial situation into a fixed category, in fact, quite the opposite. Through surveys and through successful communication tracking, the system will adapt to what is preferred by the user and what proves to be the most effective over time. This is done on an individual patient by patient basis.

The initial communications can be sent though what is thought to be the expected or deemed most typically accepted for the demographic at hand. Additional options can be presented to the user to override or change these options. As interaction with the user is established, the preferred communications can be determined from the user behavior and the methods selected to communicate.

The system also modifies the content of the initial and subsequent communications for patients. The derived context for each situation allows the system to set appropriate content for messaging as well as set the timing of communications to patients. This overcomes the many issues inherent in today's systems that revert to billing the patient the full invoice as soon as there is any issue with the expected insurance billing flow leading to confusion, frustration, and typically additional cost in either responding to patients, or in some cases loss of revenue from non-payment.

Consolidated information about the patient is gathered from various sources including manually entered data about the patient by the doctor's staff, historical data from the doctor's office Practice Management system, data entered by the patient on the patient intake prior to the appointment, and from insurance EOBs either from PM integration or through the insurance clearinghouse. This data is used to customize the content and timing of messages to tailor to a patients' needs or circumstances providing improved outcomes and a better experience.

Perhaps a patient has had extensive medical procedures resulting in large bills and costs. In such a situation, the diagnosis of the patient can be used to influence the wording and the timing of the invoices so as to be sensitive to the patients' clinical care perhaps delaying the invoice when the patient is recovering or offering payment terms. The system also analyzes the aggregate of a patient's health history, both from the doctors electronic health record software and the doctors insurance claim submissions. It can detect whether a patient suffers from communication disabilities, such as the presence of ICD-10 Diagnosis Code "H.91.90," which means the patient suffers from "Unspecified hearing loss, unspecified ear". By weighing this information with the patient's responsiveness to phone calls and other billing actions sent by the automated system in the past, and also weighing it with whatever medical procedures have been performed on the patient (e.g. treatment of his/her hearing loss or a detected "Encounter for fitting and adjustment of hearing aid" specified by ICD-10 procedure code "Z46.1"), the system performs a final statistical analysis on similar past billing cycles to decide whether it should send an automated phone call to that patient and customize the message/voice content appropriately based on these variables and how the system's user have configured their dynamic messaging preferences.

In another situation, perhaps the patient provided only their secondary insurance information at the appointment. The secondary insurer would deny the claim for the reason there is another payer on file. Rather than simply revert to billing the patient the full amount and placing the burden on the patient to find and resolve the issue, the system detects this problem and engages the patient with content specific to the situation at hand. In this case, a web form asking to validate the primary insurance is provided or specific communications to that effect is issued rather than sending an erroneous invoice. Once this information is collected, the claims are resubmitted, and the patient billed the appropriate amount.

In another such situation, a patient may have gone through an entire billing cycle process without making a payment, but throughout the process, they have been texting and emailing questions about their bill, and working towards a resolution. As the billing cycle reaches it last steps, it can modify the content of messaging based on the ongoing communications with the patient to layer in additional steps that makes sense. For instance, an additional text message might be added after all questions are resolved that says: "If we've resolved the issue, you can complete the payment on your bill to ensure your account remains in good standing. If you'd like we, can send you a final statement.". The patient can then respond to this message stating they'd like a "mailed statement" or "emailed statement", and the system would then send a bill to the patient. Again, in other systems where these systems are not integrated, the patient would likely be receiving overdue bill warnings as the questions were being answered leading to frustration and what would seem like an uncaring or unsympathetic position of the practice.

In yet another such situation, a laboratory may receive referrals from several practices to complete diagnostic testing on samples the practice had sent over. In such a situation, the patient never physically visited the lab. In many cases, the patient's insurance may not have been provided to the lab for correct billing, and normal billing software systems are triggered to send the patients bills for the full amount as if they are not insured at all. In these cases, the system would alter the messaging used with these patients to collect insurance information, then alter the algorithm once the corrected information is collected to resume a normal billing cycle workflow.

In another situation a patient's insurance is billed, but their insurance company sends a check for payment directly to the patient, rather than paying the doctor directly. When the patient's bill becomes due, the system recognizes this situation, and based on the claim's data, tailors the communication to specifically address the payment sent to the patient in the language used in the correspondence.

The above examples are provided for illustrative purposes and not meant to be limiting in any way, through the use of outcome based machine learning and adaptive algorithms the system is able to tune itself to many more situations as they occur.

Similar to how the system described herein learns and adapts based on historical successful bill collection, or historically successful communication attempts. The same techniques and systems can be employed for appointment scheduling, for follow-up care, and for many other interactions that a practice may undertake.

In typical cases, one would push or more heavily weight the choices towards recommending and preferring electronic communications if the patients are amenable to such options. Statement suppression is less expensive, environmentally friendly, and also does not require the sending of personal and health related information through the mail in paper form. Such data, when sent electronically, can be securely encrypted employ multi-factor authentication making access more secure. The practice benefits as well through saving in printing and mailing costs while also getting the information to the patient faster and more reliably thus increasing the likelihood of receiving payment and responses in a timelier manner.

Even when using paper mail outs, the system is capable of tracking mail delivery of first-class mail by tracking USPS numbers and other tracking systems to minimize any scenario of lost or misdelivered mail or returns to sender.

Another area that often adds confusion to both doctors and patients is the area of the reconciliation of the explanation of benefits with what was billed and what is covered by the insurance provider. In these situations, additional steps may be necessary for the timely explanation to patients about why they owe what they do and in order to alleviate concerns around potential billing errors or misfiled claims. For example, sending a bill to a patient for a service which they were expecting to be free would likely result in them asking questions or putting it aside to look at it later when trying to reconcile it with their insurance claims, explanation of benefits, or their insurance portal. Such tasks can easily be put aside for later or avoided altogether. Patients may get distracted, not know where to look, or give up waiting online to talk with their insurance company, or any number of similar situations. The same bill with a short explanation of why out of pockets are due could alleviate this delay, and resultant anxiety. Perhaps a note that this was due to a deductible not being reached, or a procedure not covered by their insurance, or a co-pay, would be sufficient to overcome these concerns and help them understand why they have the obligation to pay and that the obligation is legitimate. Many such questions can be anticipated and addressed proactively.

Medical billing and the reconciliation of bills with insurance coverage can be very complex for just about anyone, including those in the medical profession. This simplification of the invoicing process catering to the patient with a clear emphasis on the bottom line of what has to be paid removes much of the confusion. It quite possibly removes barriers to patients accepting procedures which are important to their health that they may otherwise hesitate about for financial reasons. The removal of surprise invoicing and a clear understanding of what has to be paid out of pocket simplifies the decision to proceed for the patient and increases the odds of collection by the provider.

Most insurance companies today offer EDI compliant inquiry and response systems using methods such as the EDI 270 Health Care Eligibility/Benefit Inquiry transaction and the EDI 271 Health Care Eligibility/Benefit Response which are constructs used to ask for and provide information about a subscriber's healthcare policy coverage. These types of systems make it possible for a system to query cost and availability of coverage before a visit and before a patient is committed to undergoing a treatment and thus obligated to pay. The knowledge of costs would relieve much of the stress and anxiety from many patients concerned about cost and coverage. A system capable of assimilating these costs and sharing a complete and overall picture with the patient would be desirable.

With the many systems involved in the billing process, and for complex processes, invoices may be coming from many sources. A system that can combine and reconcile these costs across invoices is also an important way to detect and resolve errors. This can be done before the invoice is sent to the patient alleviating any stress and confusion related to overbilling or underbilling by error. These inevitably lead to frustration by the patient and may lead to under collection or non-collection by the practice.

Today, blockchain technology, simplified as a distributed immutable ledger system, may be used to record and verify such transactions and keep a traceable and immutable record of a query and its response. One by-product of such a system is that in the future the agreed upon prices and services can be easily looked up and defended with the parties on either side of the transaction being held accountable for their side of the contract. There can no longer be a new surprise from the insurance company that they are not paying for something which was supposed to be covered, or a new charge by the practice about something not included in the estimate. Similarly the charges are outlined to the patient before treatment begins.

Doctors' practices also have a multitude of systems which are used to run the practice. These include practice management systems, electronic health record systems, scheduling systems, accounting systems, etc. In some cases, the knowledge that resides in these systems is beneficial from the standpoint of communications and billing and the ability to interact with these systems can greatly improve the success rate of such functions. For example, knowing that a patient is coming to the office for follow-up care and has a balance due could trigger the sending of a gentle reminder to them as they are coming to the office anyway. A patient that had missed his last appointment, may be subject to multiple reminders as well as potentially a reminder about an applicable cancellation fee that could be imposed. Patients that have credit cards that may have expired from the last time they were used and stored in the system could be reminded ahead of time to put these up to date to save time in checking in before seeing their doctors or receiving care.

This interaction also goes two ways, a communication system and billing system can export data directly into these other practice management systems rather than requiring double entry. This saves time, avoids data entry errors, and ultimately makes for a better experience for both the staff of the practice and the patient.

When we consider the billing flow of a patient visiting a medical facility, just like each patient, each flow is unique with a unique set of circumstances. Consider for a moment the entire history of that patient's communications, their demographics, and their prior communications and how these relate to how the patient understands their bill. We may consider each unique set of circumstances and label/codify these as billing conditions that dictate whether a billing action should be performed or not. We may modify the language and mechanism which delivers these to the patient. These billing conditions may include information about whether or not a patient has insurance, whether they are responsible for their own invoices or have a caretaker, whether they are on Medicaid, among a number of other situations.

Additional data in the billing conditions related to demographics such as age, ethnicity or languages spoken can be included as well as conditions such as a medical condition pulled from a medical record such as blindness, loss or limited hearing, or even reduced mental capacity can also play a key role.

Dynamic patient specific information about past interactions with this patient can be pulled from practice management systems or previous billing interactions with that same patient. For example, is there a balance due, are they known to pay their bills promptly, are there signs of financial duress?

Interaction with insurance systems to determine coverage and to perform adjudication also play key roles in determining the billable amounts and out of pocket costs for patients which are included on the invoices. These interactions and integrations with other systems can often be used to populate the system with data about a patient without having to resort to form filling or questionnaires about demographic data, much of the knowledge about a patient and their histories already exists in other systems and can be queried to be used in the system.

Most X12 interactions with insurance companies and clearinghouses utilize traditional information protocols such as REST (HTTP), SFTP, and MLLP (TCP), the system also encrypts each interaction with a public/private key pair utilized in addressing the interaction in a distributed hash table formed from the prior transactions. In this manner, each series of communications is packaged as a block of transactions "chained" or predicated via a cryptographic hash of the prior block. The resulting blockchain can be publicly shared amongst the payer, patient and insurance company in public/wide-area-networks, allowing the time-stamps of each event to be independently auditable without risk of secure information being compromised. Although the system utilizes a specifically permission-based proprietary network to currently share and propagate blocks, it uses an abstraction layer of adapters that make its own private blockchain agnostic to that underlying format. As many wide-area-network healthcare systems test new blockchain protocols, this agnostic format allows the system to work with any of them with adapter modifications as they evolve, and new industry standards arise.

In addition to the X12 (270/271) transactions being stored in the patient's personal series of blocks in the distributed hash table, the patient billing algorithm also encodes and encrypts its own transactions and discreet billing events securely in alternate block types. These billing events can also be extracted by any consumers of the blockchain, independently audited, and assembled into a more complete portable healthcare record that contains important billing statistics and analytics. As more partners and members of the network adapt this format and publish their own billing events blocks, the patient billing algorithm can utilize these and incorporate them into its neural network and decision trees.

Even as such, the feedback obtained by surveys is also used to tailor billing cycles as are a set of configurable defaults and overrides that can be done by the patients and the practice. For example, if a patient provides highly dissatisfied survey results, this information can be factored into calculations of likelihood to pay.

The above are all examples of data that can be included in the billing conditions record used in the invention and are not intended to be limiting in any way. Additional data can be obtained and incorporated through a system of APIs which captures data and normalizes this data as records in the system. Though these systems of API's vary greatly in network protocol, transport method, syntax, and server location depending on which external system with which the software system interfaces, data is normalized to the system's own platform independent relational database structure to guarantee referential integrity across patient populations in a 3NF (Database Third Normal Form) format. Asynchronous jobs constantly push and pull this data both to and from these 3rd party API's via extensible plugins that vary depending upon a biller client's configuration. These plugins can also write and read to independent blockchains to ensure auditability and interoperability.

Of course, conditions about a patient may be quite fluid and changing. A patient may change or discontinue their insurance, or a patient that had been paying promptly for many years may suddenly find themselves in a situation with a lost job, or a family financial emergency where they become slow to pay. Here, the system would take into account the long history of successful payments and a temporary change would not automatically move to a more aggressive stance of demanding payments in advance or sending an account to a collection agency. Similarly, a patient that may have missed a payment or two who becomes responsible will have their own score in the system improve over time and the billing cycle would adapt accordingly with the improved score. These life changes can be captured through voluntary disclosure from patients as well as being captured from external systems and feeds such as LinkedIn, Facebook, Zillow among others.

The system works with queues of billing conditions for patients and creates corresponding billing actions relating to the events above that result in actions being taken. While billing conditions are wide ranging and may be unique from one patient to another, the billing actions are taken from a set of available actions that can be taken and are, generally speaking, a narrower set of broader categories. The billing actions include actions such as sending of an email, an SMS text, a letter, an automated phone call, a manual call, or an internet-based chat message (e.g. Intercom, Facebook Messenger, Twitter). The details of each may of course get very specific and in the case of letters being sent might include invoice information specific to a patient, a reminder to update credit card information on file, or simply a notice that some amount of the invoice was not covered and that a deductible is due. The billing action taken in these cases should be considered as the instructions that initiate the act of sending of the message or the means used in contacting of the patient.

Combining the billing actions and billing conditions create records in the system which are placed into a billing action queue that feed into a billing cycle. These events are the combined cause and effect of the billing conditions and the billing actions listed above. The billing cycle generates a series of actions which may trigger multiple phone calls or messages to the patient and the practice. The goal of the billing cycle is to obtain a successful payment, and the cycle may include repeated attempts separated by a predefined wait interval and predefined (but customizable) messaging in each communication. For example, we may attempt three phone calls, separated by 7 days, and 3 days respectively, with an increased sense of urgency in the words chosen for the communication. The initial phone call may be a gentle friendly reminder, the second a more urgent reminder about the importance of contacting the biller, and the third and final message may suggest further action to be taken unless contact is made. These are of course only examples, and each practice can customize the contents and the frequency of the messaging using predefined templates provided in the system.

The system manages these billing cycles based on the customizable templates and sends progress information to the practice and/or biller throughout. The level of interaction and reports is again configurable. When resulting in a successful payment, the cycle completes but the historical success of the method is recorded back in the system and used to improve future cycles for the specific patient and also for similar demographics.

It should be noted that the billing cycle does not necessarily limit itself to a single means of communications. In the example above, say the three phone calls had not resulted in successful payment collection, then, after the 7 day and 4 day retries with phone calls, the same billing cycle may resort to sending a letter and waiting say 30 days, or 7 days after the USPS signaled delivery of the letter. The template may then send a second letter, and if no payment is received, send yet a third letter. Again, these letters may get increasingly urgent in the contents and the amount due may also start to accumulate interest or penalties. The system may also alternate communication methods as defined in the template to send a letter, and then follow that up with a phone call after receiving confirmation of delivery or waiting a predetermined amount of time. In any event, the billing cycles should be considered flexible and configurable. They are designed to be persistent with escalating urgency. They are also feeding in success and failure data back into a machine learning process to improve and adjust the templates used for each patient's specific billing cycle.

The dispatching of communications, statements and balance reminders is done through a programmatic algorithm also managed by a neural network incorporated into the system. The system uses an adaptable and self-adjusting set of heuristics and tunes itself using both successful payment and communications events as well as user input and demographic based default values. Users deemed to be similar by the system may be treated in similar ways. If a certain set of actions has been successful on one patient to get them to respond to a query this same set of actions may be applied to a different user that has been deemed unresponsive using other means. This specific process of adapting and duplicating the parameters and ordering billing events that historically lead to successful payments in similar cohorts of patients generates a unique self-correcting network that displays an emergent artificial intelligence unlike any prior billing communication platforms.

The current manifestation of the system incorporates communications methods popular at the time of writing such as paper statements, text messages, internet-based chat software (e.g. Intercom, Facebook Messenger, Twitter), SMS statement reminders, automated and manual phone calls, physical mail, and indirect mail to authorized caregivers. It should be noted however that the system can be expanded to include other means of communication and interaction as they become available including new means such as blockchain contracts, social media notification events, or others as they become popular and available.

While it is possible for a practice to perhaps set reminders to follow-up with patients, the level of repeatability and consistency in the system being described would be impossible to perform manually. Further, the machine learning capability on a per-patient basis is again something which any normal medical practice or billing company managing a large number of patients could never do manually. To perform this level of individual tailoring of billing cycles which learns through experience of dealing with each patient individually is beyond the scope or capacity of existing systems or any manual process. Due to the subtlety of these changes, the size of the data set, and the real-time responsiveness of the adaptations and alterations, doing even one these parameter adjustments or patient comparison operations manually would be impossible; whereas the system's relational database queries make it possible to do several thousand per hour. The statistical analysis done on each billing condition, event, and action of the billing cycle, as well as the neural network that dictates their evolution over time, requires the unique indexing, relational data structure, and computing power described in this document.

In accordance with one embodiment, a method is provided for setting up a preferred profile of communications preferences. A menu of available choices such as email, SMS, phone calls, internet-based chat software (e.g. Intercom, Facebook Messenger, Twitter), or paper as available and are selectable. This process can be performed by the patient or the provider and walks through a series of menus to set the preferences of a particular user. Interactions and integrations with other systems can also be used to populate the system with data about a patient without having to resort to form filling or questionnaires about demographic data, much of the knowledge about a patient and their histories already exists in other systems and can be queried to be used in the system and this is the preferred method. The system assigns defaults to patients based on demographics and this process is further outlined in FIGS. 1 through 4.

Figure 5:
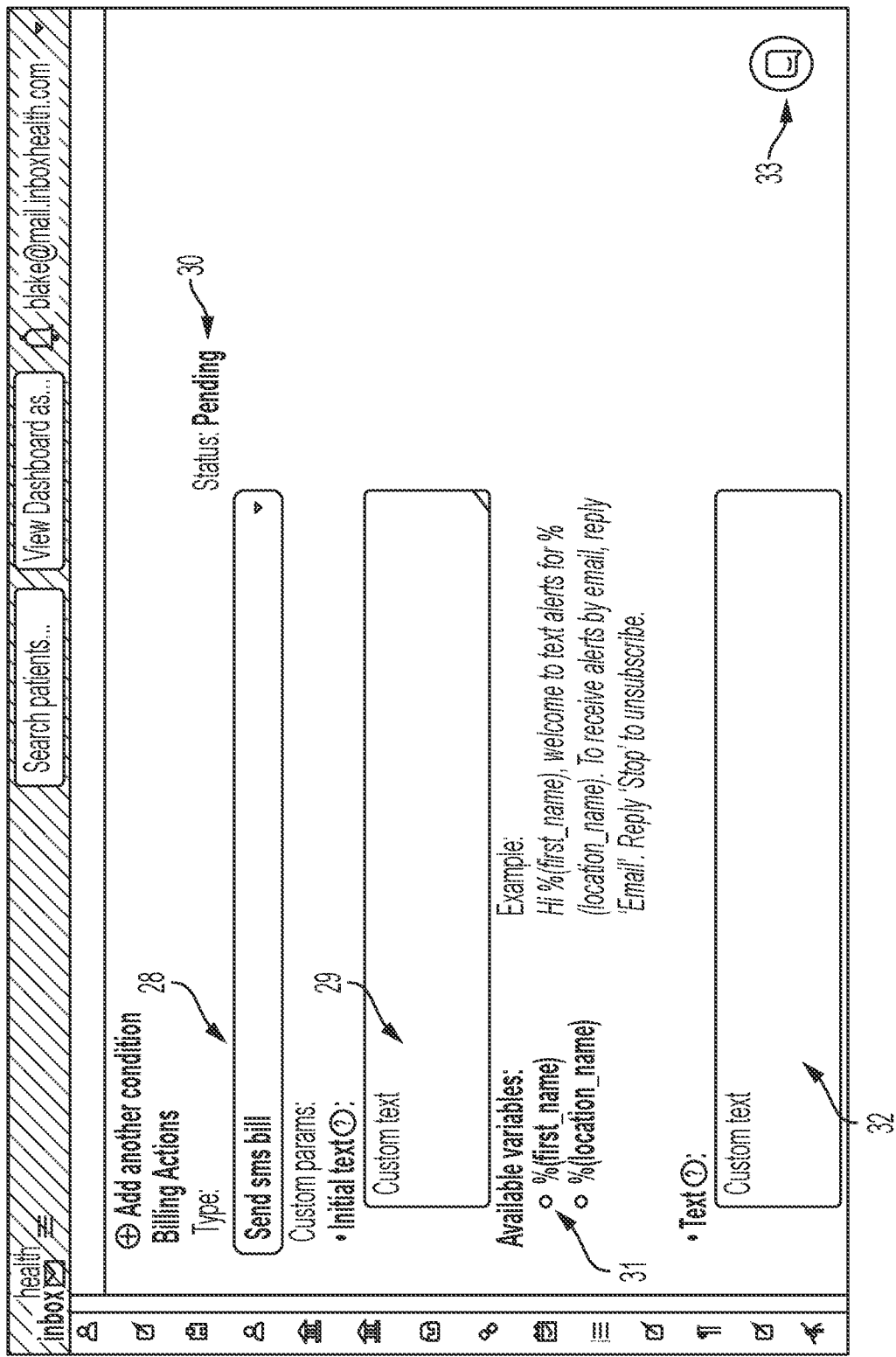
FIG. 5 is an example web portal where customized communications can be overridden or manually edited.

In accordance with another embodiment, a method is provided for overriding the default contents of messages. A search and select process is provided to find particular items in the process queue as depicted in FIG. 5. A data entry screen is provided to update the various fields including the communication preferences as well as the content of the message. Allowances of the addition of custom content are also provided.

In yet another embodiment, a method is provided for prefilling patient agreements and filling in demographic information. This process lets patients enter this data at their convenience, in the privacy of their homes and without having to fill paper forms which are later transcribed and subject to human errors and possible unsafe handling of these.

In yet another embodiment, the asynchronous billing cycle creation module denormalizes, tags, and optimizes all data entered by either the medical biller, healthcare professionals, or the patient themselves into the front-end user interface. This organized data, stored structural in a relationship database, serves as the basis for the generic billing cycle algorithm as it generates new billing conditions, and modifies the billing actions based on success criteria.

In yet another embodiment, all appointment data is read from the practice management system via means such as API calls, the polling of external systems or other data exchange methods to capture any updated or changed appointment information. The application also provides a user-interface for patients to schedule and change their appointments to desired time-slots that match with both the availability of providers and their working hours. Based on the patient's feedback the user interface displays slots sorted according to the parameters they desire. The billing algorithm later utilizes this access to real-time appointment data not only to provide patient customized notifications within their billing cycle, but also allows the practice or biller users, who have opted-in to this feature set, to enable insurance eligibility checks that automatically utilize the platform's connectivity to insurance clearinghouses (usually through an API or VPN-based TOP socket) and check their out-of-pocket expenses in real-time against a fee schedule for that provider. This information is parsed through layers of custom programmatic parsers and displayed such that the application's user interface for the biller, practice manager, and patient to view through their respective portals at any time.

Though important to the end-users and the overall patient billing experience, viewing, scheduling and communicating these insurance eligibility checks has been automated by several systems in the past such as U.S. patent application pub, no. 20110313784 by Harvey; David D, et al. However, the present system utilizes the patient's information and history to customize and tune discount payment plans to the particular patient demographics and subsets based on user settings and defaults, then uses an appropriate averaging method (usually a Gaussian distribution) on prior successes to influence and suggest further modifications to biller end-users. This adds an additional layer of machine learning to the financial modelling of the patient's payment plans that can be customized within each dynamic billing cycle. For example, after computing average deductibles for a particular patient set, the system can flag particularly high deductible patients, subtract the configurable allowable threshold for discounted payment plans, then present new payment plan options to the patient while they go through the check-in or patient portal components of registration, health history, and/or check-out. During this presentation step, the system alters a dynamically customized contractual financial agreement (based on the values in the latter step) and presents a secure credit card entry form alongside it. Once the patient has agreed to this special financial agreement, the system schedules the payment plan asynchronously, and the patient's accounts are automatically debited at the optimal date intervals for both the patient and the healthcare biller using the asynchronous job queuing system.

Figure 2:
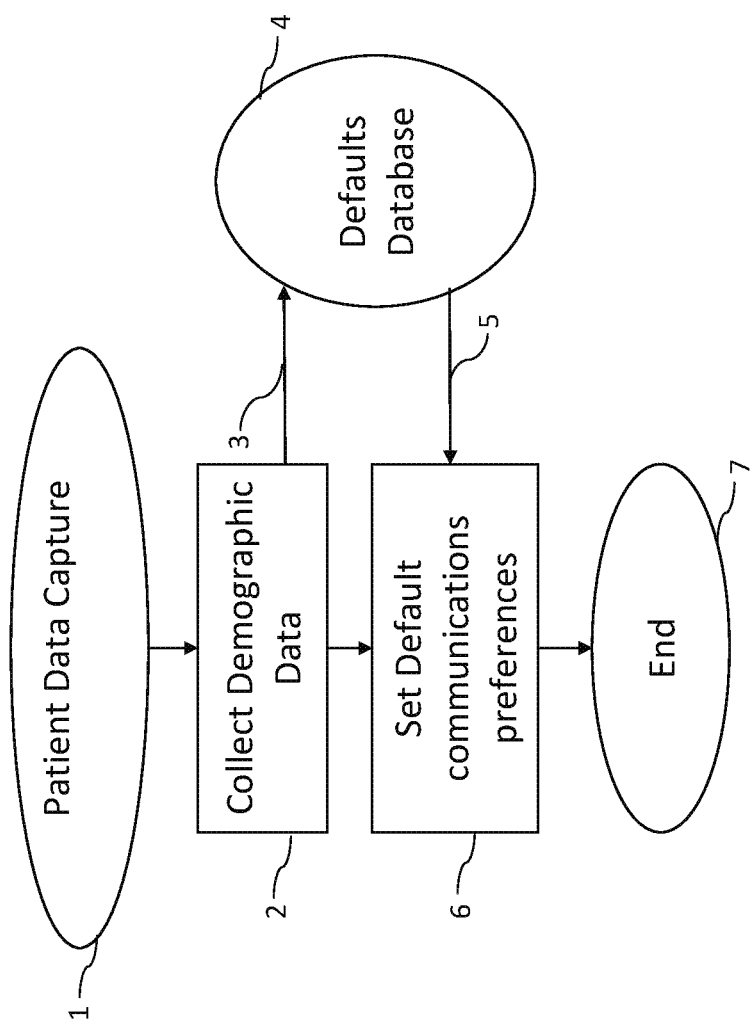
FIG. 2 is a functional flow diagram showing patient data capture, communication and preference setting according to the present invention.

Turning to the drawings, FIG. 2 shows a logical flow of the patient data capture process and the gathering of the demographic data and the setting of the defaults. Here the patient demographic data is captured through interactions and integrations with other systems and is used to populate the system with data about a patient (1) This data can also be entered by either the patient, a caregiver or the provider. Demographic data is collected and entered (2) and this data is then sent to (3) the defaults database (4) which may be part of the storage (120). The defaults database (4) is then queried to find communications preferences for the demographic which serve as default values to be used for the patient and these are sent (5) and stored in the patient record and set as default communications preferences (6) which ends the process (7).

Figure 3:
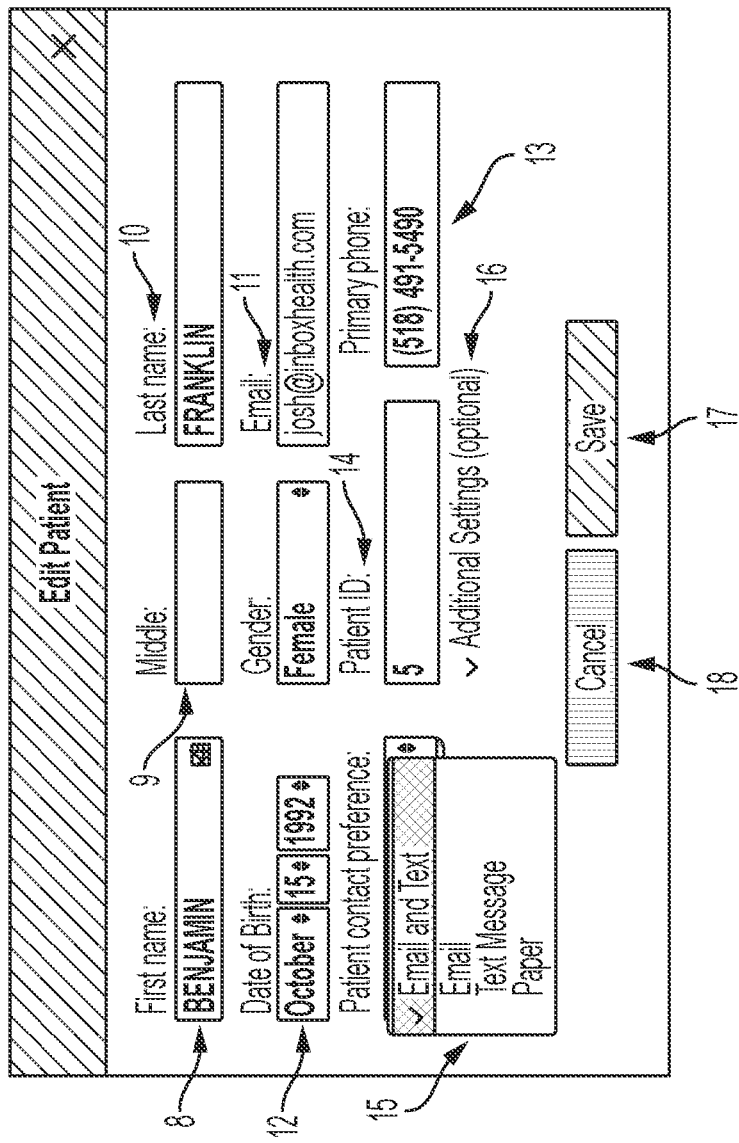
FIG. 3 is an example portal for patient information editing according to FIG. 2

Turning now to FIG. 3, we see a sample patient contact preferences screen which can be used to override defaults or set preferences in the system. This data entry screen can be displayed on a mobile device, tablet, or computer system or webpage or equivalent. It is made up of data fields such as the patient's first name (8), middle name (9), and last name (10). The screen also includes the email address (11), date of birth (12) the phone number, (13) and the patient's gender (14). Additional settings for demographic data can be expanded in additional screens through a selection for additional settings (15). The contact preference is selected from a set of available options in a pull-down menu shown as a sample contact preference (15). Finally, once filled the patient or provider editing this screen can save (17) the settings or cancel (18) out of the screens.

Figure 4:
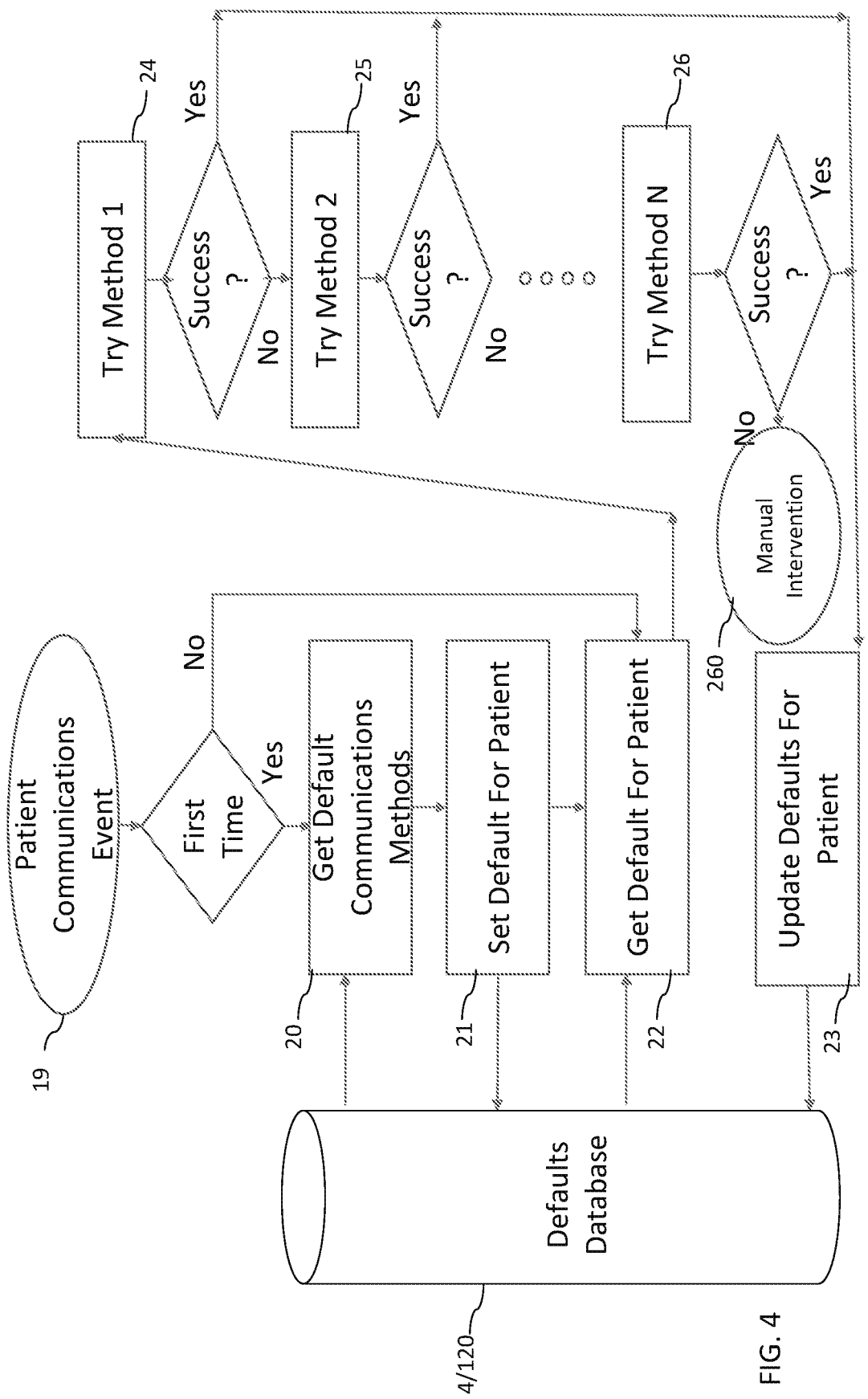
FIG. 4 is a more detailed functional flow diagram showing the communications process of the present invention.

FIG. 4 shows the logical flow of the system in operation once the patients have registered and the system is processing events. Here, a particular patient communication event is triggered (19) and we look at see if this is the first time a communication is to be sent to the patient. If so, the default communication method (20) is obtained from the defaults database (10) and then set for the patient (3). If the patient has already been communicated with before, the system may have modified the communication preference based on success or failure criteria of past transactions so the default communication method (22) is obtained from the database (10).

In either case, whether it be the first time or a repeat occurrence, the system now has the default communications method and will attempt communication with this, as method 1 (24). Should this method be successful, the default is again updated or confirmed (23) in the database (10). If not successful, the system will go on to attempt other methods (25)(26), as outlined in a ranked and weighted selection process in the system to attempt to communicate with the patient. If any of the subsequent methods (25)(26) are successful, again the default is again updated or confirmed (23) in the database (4)/(120). However, if unsuccessful, the system will generate errors or warnings and manual intervention (260) may be necessary to contact the patients or take remedial action. These remedial or "no response" billing cycles get enumerated in the user interface, where billers can select write-off options or forward them to one of the collection agencies integrated into the platform. After the charges are written-off or moved to the collection agency, the platform also posts these updates and write-off directly to the practice management system used for account purposes.

Turning now to FIG. 5, we see a method to override specific content generated by the system. Billers, Administrators, and/or Providers can find existing billing actions in the system and open these, Notice the status (30) is set to pending and this message has not been sent yet. One can see, and or update the fields including the action (28) which is the billing preference, the actual text or content of the message (29). Variables can be added as shown in (31) using variable replacements for fields such as the names, dates, or locations that are stored in the database. Custom text (32) can be added to the message, and, when completed, the send icon (33) is pressed to complete the modification.

Figure 6:
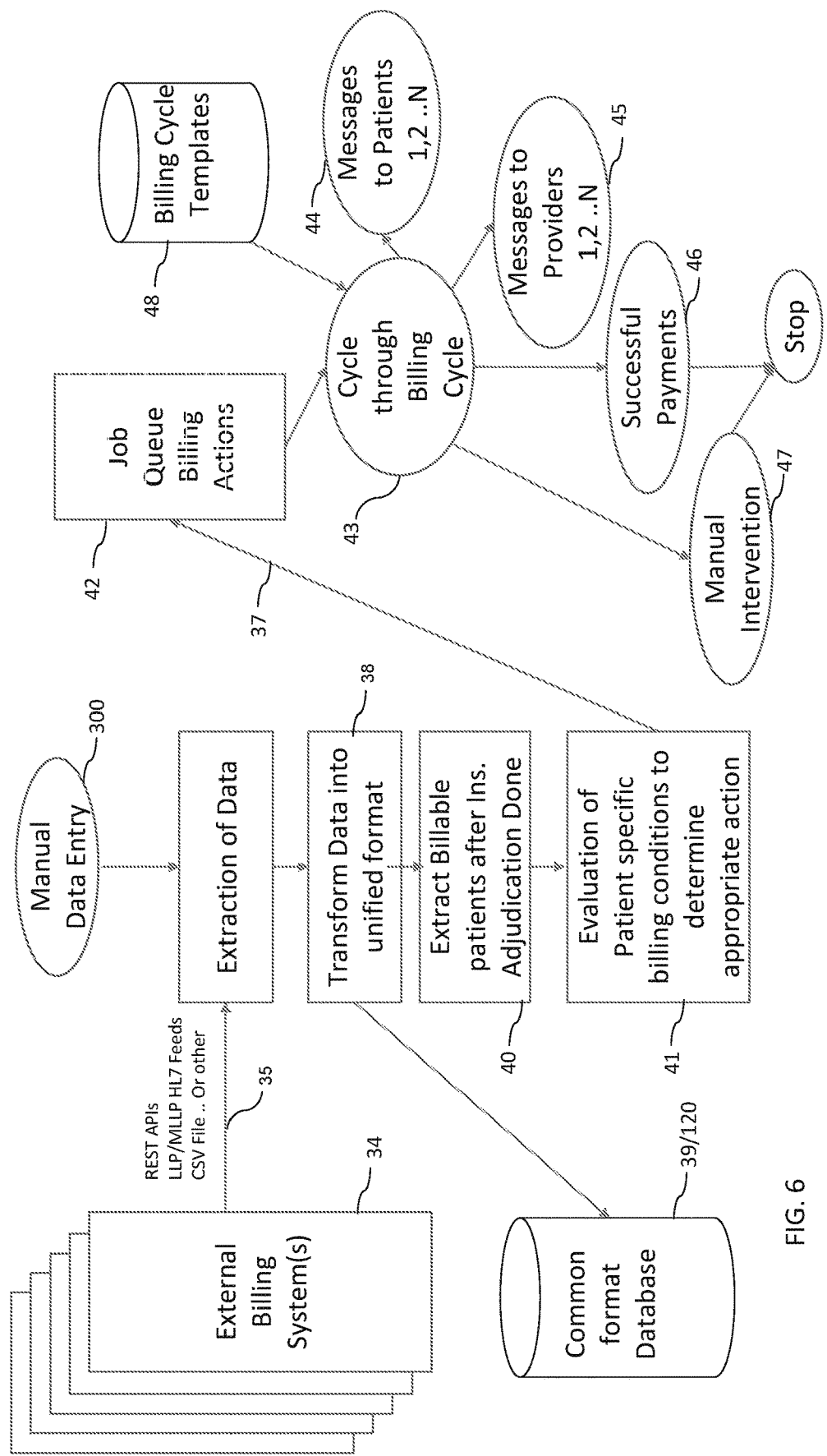
FIG. 6 is a more detailed functional flow diagram showing how patient data is obtained and transformed and then used for communicating with the underlying users.

Turning now to FIG. 6, we see the inputs to the system in terms of data from external billing systems (34). This data is extracted and pulled or pushed from these systems in a number of ways including but not limited to Rest APIs, LLP or MLLP methods for sending HL7 feeds, CSV Files or others (35), each of these formats can be extracted (37) into the system for processing. There is also an option for manual entry of data (300). The system then transforms the data (38) into a unified format or content and stores this in its working store (39) which may be a database or other form of storing records (and may be part of storage 120). Once in this unified format, the system looks for and extracts billable patients, which are patients with an outstanding balance post insurance adjudication (40). These patients are then evaluated based on the default data known about the patient (41) including the prior interactions and defaults for the categorization of patients in a particular demographic and placed into a job queue (42).

The job queue of billing actions (42) feed data to one or more workers that cycle through the billing actions in what is called a billing cycle (43) and generate communications with the appropriate frequency sending messages to patients (44) as well as to providers (45) leading eventually to successful payments (46) or manual intervention (47), The cycle may repeat multiple times sending increasingly urgent messages and cycling through a variety of communications means as defined in the billing cycle template (48) (which may be stored in storage 120. When successful payment is received (46) or when all attempts in a given cycle (43) as defined by the template (48) are exhausted then the system will halt calling for manual intervention (47)

Figure 7:
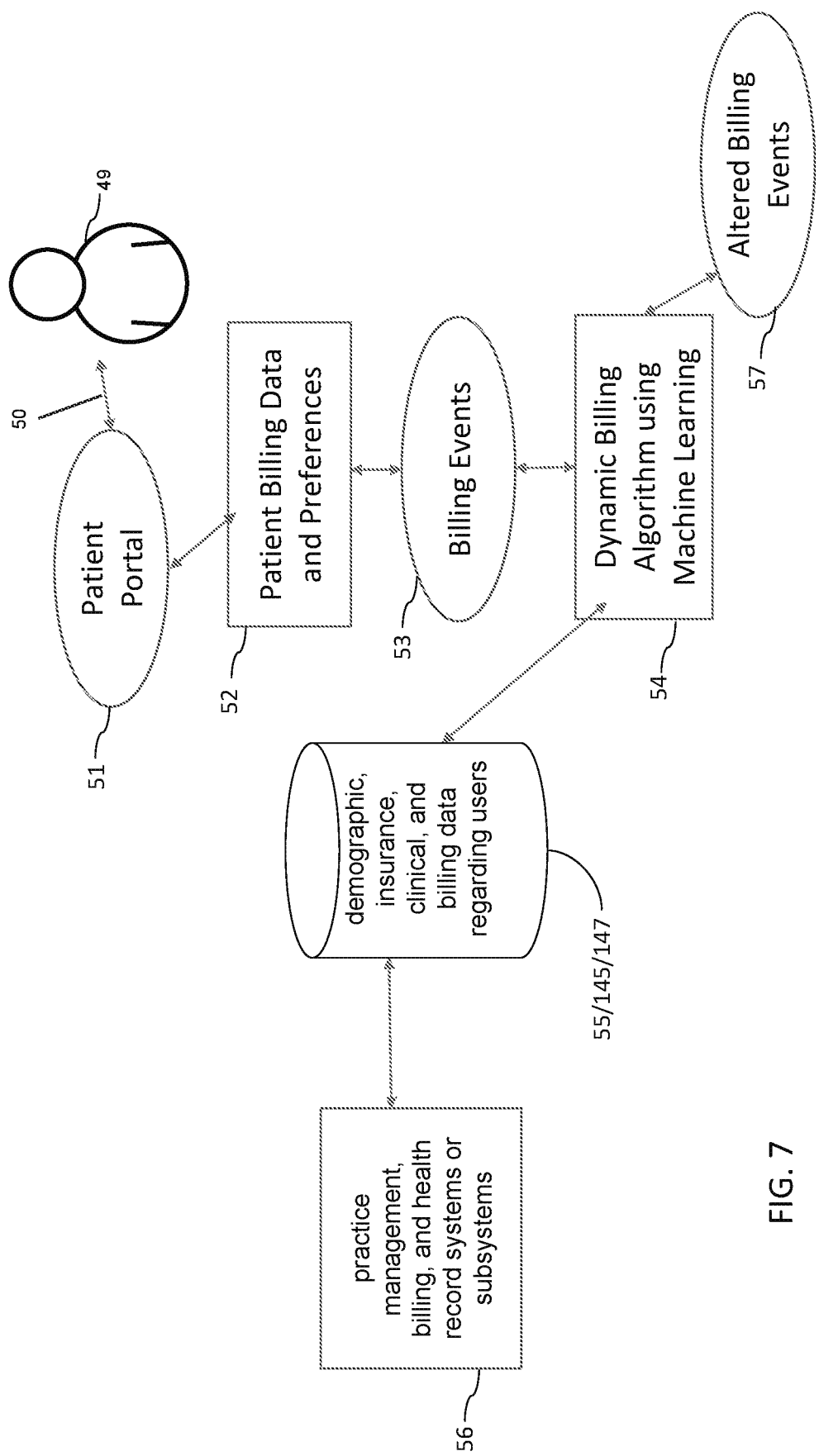
FIG. 7 shows a functional flow diagram of how billing events are altered based on available data.

Turning now to FIG. 7, we see a view of creating altered billing events using a dynamic billing algorithm. A user or patient (49) communicates (50) with a patient portal (51). This communications can be done via any means, be that a voice call, an email, a text, or a written letter later scanned and converted to electronic form. Patient Billing data and preferences (52) are used to create billing events (53). These billing events are fed into the dynamic billing algorithm (54) which uses machine learning combining demographic, insurance, clinical and billing data regarding users (55)(145/147) which is obtained from practice management, billing, and heath record systems (56) and may be stored in storage 120. The Dynamic Billing Algorithm using machine learning (8) then creates altered billing events (57) which are used to communicate with the patient. It is understood that the dynamic billing algorithm can be made up of the actions done by one or more of the patient data module 142, defaults module 144, history module 146, insurance adjudication module 148, medical module 152 and data module 156.

Figure 8:
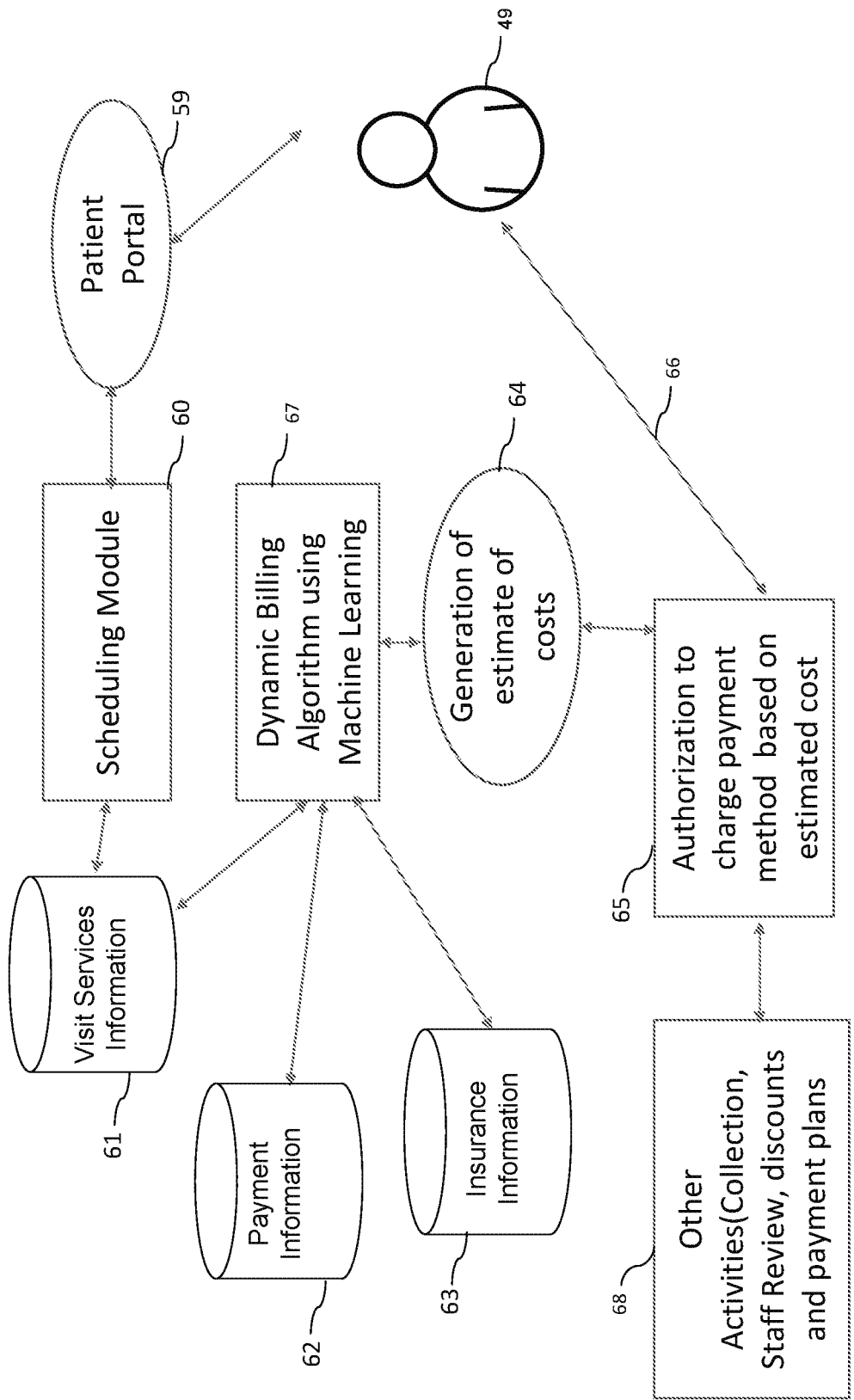
FIG. 8 is a functional flow diagram showing how pre-visit estimates and authorization is obtained.

Turning now to FIG. 8, we see an overview of how the invention determines estimates and authorizes payments. A user or patient (49) communicates (58) with a patient portal (59). This communications can be done via any means, be that a voice call, an email, a text, or a written letter later scanned and converted to electronic form. The patient portal provides access to a scheduling module (60) which takes appointment information from the patient. This information includes appointment date and time information but also information about the nature of the visit. This information about the visit is matches with Visit services information (61) and used by the dynamic billing algorithm using machine learning (67) which also takes as input data from payment information (62) which may include if/when the user pays their balance and insurance information (63) such as insurance adjudication codes and associated reasons for approval/denial. The visit services information 61, payment information 62 and insurance information 63 may all be stored in the storage 120 in a unified format as part of the overall contact 145 and/or patient 147 data. Similarly, users 49 who utilize services which were recently billed to another user with the same insurance can be queried to determine expected costs. This is combined to generate an estimate of costs (64) which is then creates an authorization form (65) for payment which is presented (66) to the patient (49). This data can also generate other actions (68) such as collections, staff reviews, discounts and payment plans which may also be used to generate a different authorization (65) presented (66) to the patient (49).

Figure 9:
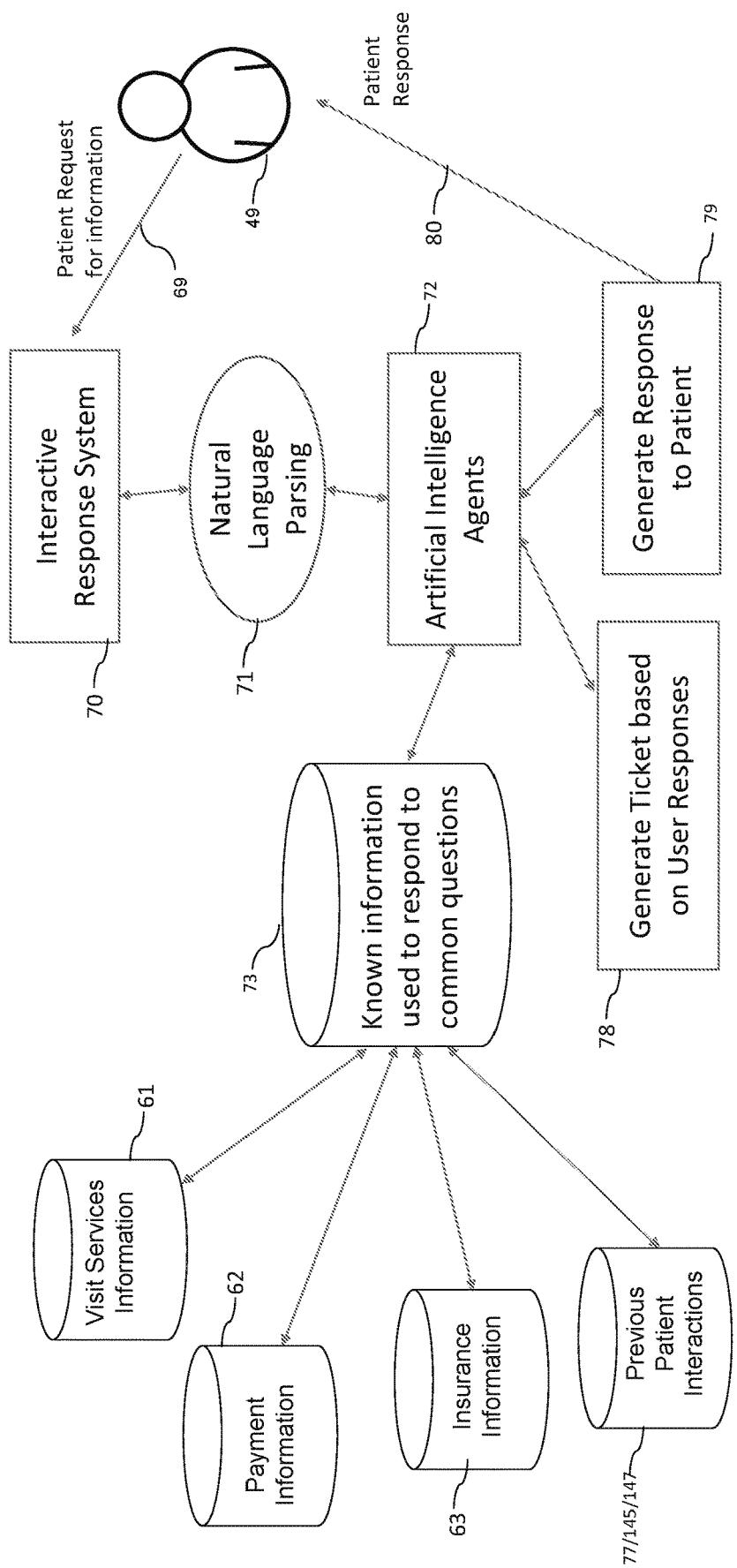
FIG. 9 shows a functional flow diagram of how patient communications can be automatically handled.

FIG. 9 shows a view of how natural language processing is used to parse and interact with patients and create tickets, A user or patient (49) communicates with an interactive voice response system (70) sending a request for information (69). This request is run through natural language parsing (71) and fed to an artificial intelligence agent (72). This Artificial intelligence agent (72) as access to data about known information related to common questions (73) which is in turn generated from prior visit services information (61), payment information (62), insurance information (63) and previous patient interactions (77/145/147). The Artificial Intelligence Agent (72) generates a response to the patient (79) which is turn communicated (80) to the patient (49). This response or other artifacts of the process can also be used to generate a ticket (78).

Figure 10:
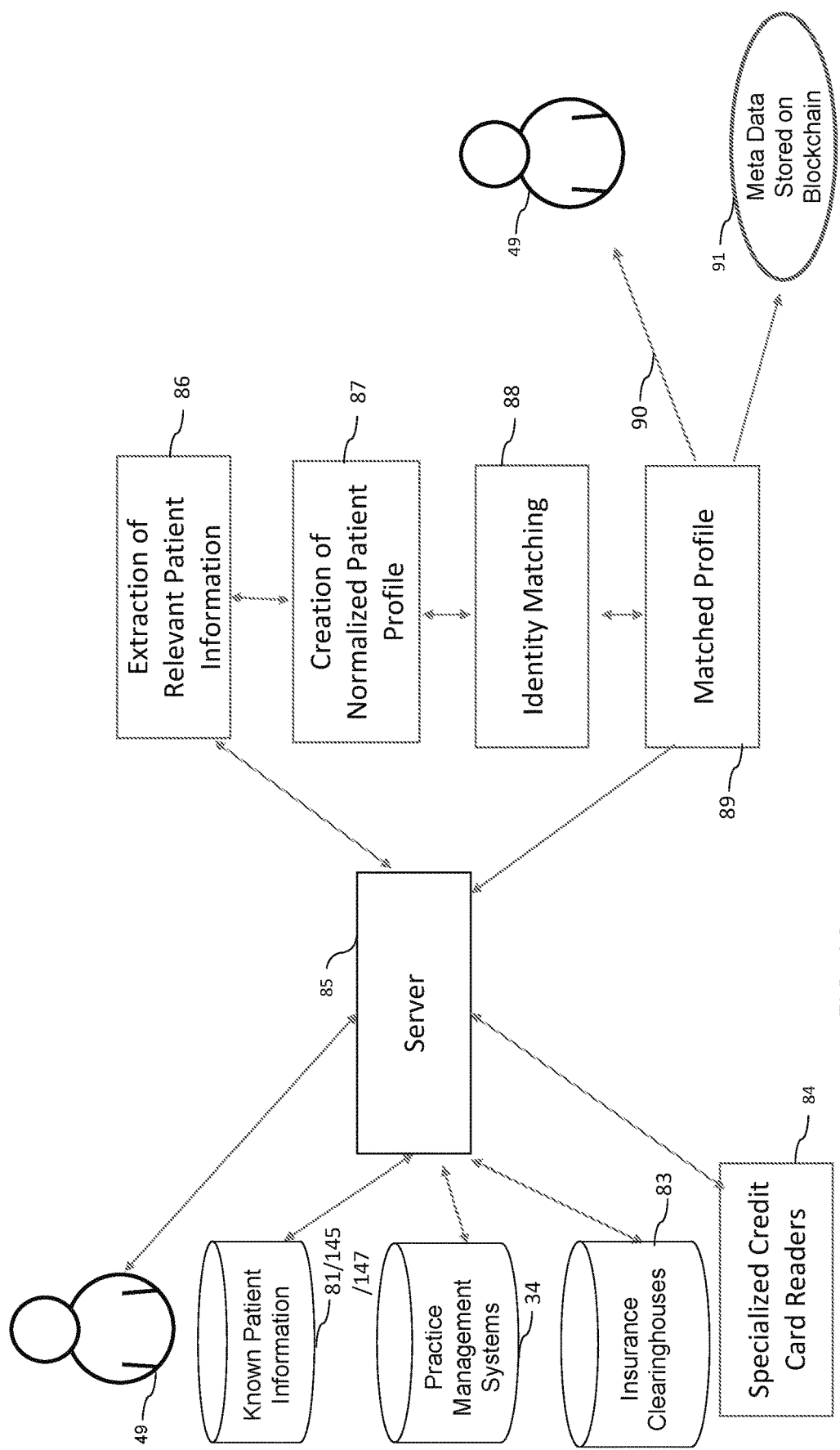
FIG. 10 shows how patient data can be obtained from a variety of sources in order to optimize communications and bill collection success.

FIG. 10 shows how the system matches disparate data into a matched profile doing identity matching and communicating with disparate systems and users. Here a server (12) communicates with and collects data from (49) patients, systems containing known patient information (81), practice management systems (82) and insurance clearing houses (83), The server (85) software can also pull data from specialized credit card readers (84) that may be in the offices or manual processing where interactions with automated systems is not available. The server (85) extracts relevant patient information (86) and created a normalized patient profile (87) recognizable to the server and the system in an internal and standard format. This profile is then identity matched (88) arriving at a matched profile (89) which information about billing preferences and communication preferences are known. This information can now be used to contact (90) a user or patient (49) and metadata can be stored on a blockchain (91) for safekeeping and transparency.

Figure 11:
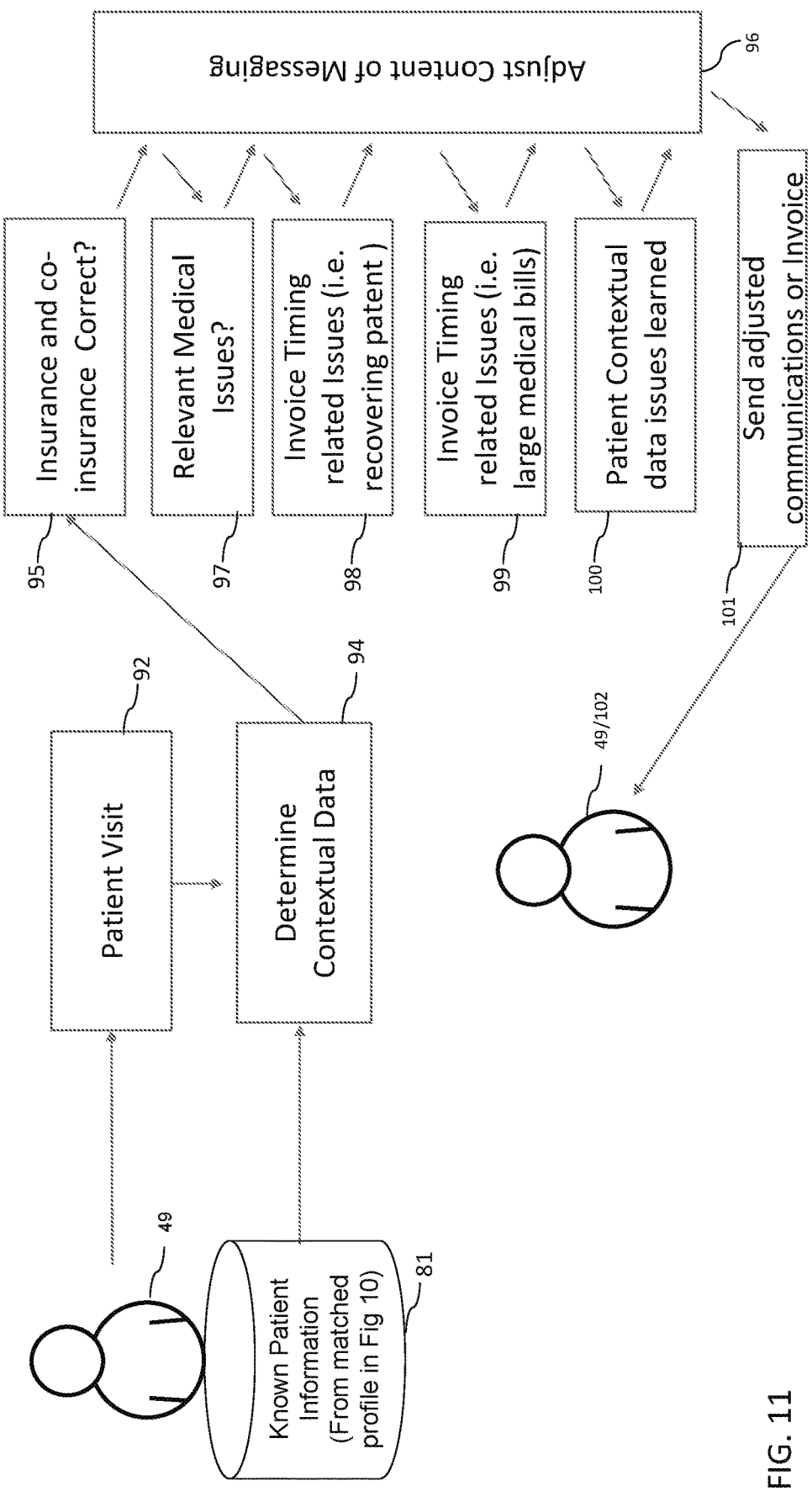
FIG. 11 shows a functional flow diagram of how message content is provided customized context for particular users.

Turning now to FIG. 11, more detail on an embodiment of the algorithm of FIG. 1 is shown. We see a user (49) that goes to a patient visit (92) at a medical practice, Known patient information (81) is pulled from the various systems as was highlighted in FIG. 10 and is understood to include data described as part of the storage 120. This known patient information (81) is used to determine the contextual data (94) about the patient. Knowing this contextual data (94) a series of decisions are made such as whether or not the insurance and coinsurance are right (95) and if not, the adjusted communication/invoice 101 is modified in content 96 to e.g. ask for updated information. Going down the decision tree, a check for any relevant medical conditions (97) is made and if any exists then again the content of the messages used to communicate are adjusted (96) to reflect this. Again continuing to parse any relevant contextual information checks are made regarding invoice timing such as whether the patient is in active recovery (98) which can be determined by the medical module. Or, if the patient is facing large medical bills (99) the messaging can be adjusted (96) to reflect these circumstances. For example, large medical bills can indicate that a payment plan should be proposed to the user. Additional contextual data is learned by the system based on the outcomes of previous interactions and the system is adjusted to alter timing and content accordingly (100) based on the history module and data module which updates the storage 120 with various results and outcomes from user interactions. Finally when all known and learned context checks are made (95, 97, 98, 99,100) and the message is adjusted taking these into account (96), a final communication is prepared (101) and send to the designated recipient (49/102) who may be the patient (49) or another person chosen by the patient. This final communication will typically be the first time the user 49 receives the bill for the particular visit or services utilized and the communication will typically provide various options to pay including by check, credit card, ACH transfer, cryptocurrency or other forms of payment. As payment receipt is tracked by the same system which sends out the communication (with the bill), the success of the communication can be efficiently determined so that duplicate bills are not sent and so that those bills which are outstanding are worked on and eventually highlighted for possible manual intervention as needed when the balance becomes long outstanding.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A patient communications system comprising:
a storage containing contact data related to the plurality of patients, the contact data indicative of communications habits of the plurality of patients as related to bill collection success;
software executing on a computer wherein the software comprises a machine learning program which determines how to communicate with a patient user, the machine learning program receives patient data indicative of contact, insurance and demographic information for a plurality of patients, one of which is associated with a patient user;
the machine learning program further queries the contact data and patient data to determine a rank order of communications methodologies based on the communications habits of the plurality of patients as compared to the demographic information;
the machine learning program further queries the storage by the patient user to determine modifications to the rank order of communications based bill collection success for the patient user;
the machine learning program further queries an insurance adjudication result to determine one or more codes which are related to a bill associated with the patient user;
the machine learning program further queries the bill based on one or more patient treatment codes associated with a change in likelihood of one or more communications methodologies being successful, the software updating the rank order if the one or more patient treatment codes indicate a change in likelihood with one or more communications methodologies in the rank order of communications; and
the machine learning program further generating a bill communication for the patient user to transmit the bill to the patient user and further modifying a content of the bill communication based on the one or more codes to request information from the patient user if the one or more codes indicate that patient data from the patient user is missing which could modify the bill;
wherein the software sends the bill communication to the patient user using a first communications methodology from the rank order of communications and the storage is updated by the software based on if the bill is paid.

2. The system of claim 1 wherein if the bill is not paid, the bill communication is sent to the patient user using a second communications methodology from the rank order of communications and the storage is updated by the software based on if the bill is paid following communication of the bill to the second communications methodology and the storage is updated by the software based on the first communications methodology being unsuccessful.

3. The system of claim 1 wherein the software is in communication with a plurality of external billing systems, the data module extracting data from the plurality of external billing systems and transforming the extracted data to a unified format.

4. The system of claim 3 wherein the data extracted to the unified format is stored in the storage.

5. The system of claim 4 wherein the contact data and the data extracted is stored in the storage in the unified format.

6. The system of claim 1 wherein the patient user is one of the plurality of patients.

7. The system of claim 1 wherein when the one or more codes indicates denial of a claim based on expired or incorrect insurance information, the message content includes a request for updated insurance information from the patient user.

8. The system of claim 1 wherein the software modifies a communications methodology for the communication based on the one more patient treatment codes.

9. A system for generating customized patient billing communications comprising:
software executing on a server which receives patient billing data indicative of a patient visit and further indicative of a balance;
said software accessing a storage to determine patient visit context data indicative of one or more visit codes associated with the billing data;
said software generating a communication for a patient user based on the patient visit context data with message content altered from a standard message based on the one or more visit codes, the communication further including a bill for the balance in addition to the message content and the communication being a first communication to the patient user with the bill;
wherein the one or more visit codes include one or more patient treatment codes and the software modifying a communications methodology for the communication based on the one more patient treatment codes;
wherein the patient user is associated with a rank order of communications methodologies of anticipated bill collection success and the software determines a modified rank order based on the one or more patient treatment codes;
wherein the software sends the communication to the patient user according to the modified rank order;

said software updating the storage based on if the bill is paid in response to the communication so that based on bill collection success and when accessing the storage to determine patient visit context data and/or communication methodology for future communications, the software gives greater weight to the communication methodology and/or altered message content which is/are associated with actual bill collection success so that the software learns for future communications based on data in the storage indicative of the bill collection success in response to the communication methodology and/or altered message content.

10. The system of claim 9 wherein the one or more visit codes include one or more insurance adjudication codes which are indicative of how the balance was determined.

11. The system of claim 10 wherein when the one or more insurance adjudication codes indicates denial of a claim based on expired or incorrect insurance information, the message content includes a request for updated insurance information from the patient user.

12. The system of claim 9 wherein the software modifies the communication methodology to delay sending the communication based on the one more patient treatment codes.

13. The system of claim 9 wherein the rank order of communications methodologies and modified rank order are determined by the software based on the patient billing data.

14. The system of claim 9 wherein the software receives at least some of the patient data from one or more external billing systems in one or more formats and stores the patient data in the storage in a unified format.

15. A system for generating customized patient billing communications comprising:
software executing on a server which receives patient billing data indicative of a patient visit and further indicative of a balance;
said software accessing a storage to determine patient visit context data indicative of one or more visit codes associated with the billing data;
said software generating a communication for a patient user based on the patient visit context data with message content altered from a standard message based on the one or more visit codes, the communication further including a bill for the balance in addition to the message content and the communication being a first communication to the patient user with the bill;
wherein the one or more visit codes include one or more patient treatment codes and the software modifying a communications methodology for the communication based on the one more patient treatment codes and sends the communication to the patient user;
wherein the patient user is associated with a rank order of communications methodologies of anticipated bill collection success and the software determines a modified rank order based on the one or more patient treatment codes;
wherein the rank order of communications methodologies and modified rank order are determined by the software based on the patient billing data;
wherein the patient billing data is obtained from a plurality of external billing systems and the software transforms the patient data obtained from the plurality of external billing systems into a unified format, such that the patient billing data is stored on the storage in the unified format.

16. The system of claim 15 wherein the rank order of communications is determined by the software by comparing patient billing data of the patient user to other patient data based on one or more matching demographic categories.

17. The system of claim 16 wherein the storage is updated based on the patient user's communications history as related to collection success.

* * * * *